(12) United States Patent
Lewis et al.

(10) Patent No.: US 9,249,165 B2
(45) Date of Patent: *Feb. 2, 2016

(54) SLURRY PHASE DIRECT SYNTHESIS OF ORGANOHALOSILANES FROM CYCLONE FINES

(71) Applicant: Momentive Performance Materials Inc., Waterford, NY (US)

(72) Inventors: Kenrick Martin Lewis, Flushing, NY (US); Yanjun Zhu, Dobbs Ferry, NY (US); Abellard T. Mereigh, Mt. Vernon, NY (US); John Razzano, Waterford, NY (US); John David Neely, Clifton Park, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,625

(22) Filed: Aug. 28, 2014

(65) Prior Publication Data

US 2015/0065740 A1 Mar. 5, 2015

Related U.S. Application Data

(60) Provisional application No. 61/871,962, filed on Aug. 30, 2013.

(51) Int. Cl.
*C07F 7/12* (2006.01)
*C07F 7/16* (2006.01)

(52) U.S. Cl.
CPC .... *C07F 7/16* (2013.01); *C07F 7/12* (2013.01)

(58) Field of Classification Search
USPC ................................. 556/466, 472, 473, 474
See application file for complete search history.

(56) References Cited

U.S. PATENT DOCUMENTS

| | | | |
|---|---|---|---|
| 2,803,521 A | 8/1957 | Nitzsche et al. | |
| 2,904,574 A | 9/1959 | Kohn et al. | |
| 4,224,297 A | 9/1980 | Straussberger et al. | |
| 4,328,175 A | 5/1982 | Roeckel et al. | |
| 4,328,353 A | 5/1982 | Shah | |
| 4,330,510 A | 5/1982 | Schauer et al. | |
| 4,390,510 A | 6/1983 | Ritzer et al. | |
| 4,454,077 A | 6/1984 | Litz | |
| 5,338,876 A | 8/1994 | Jung et al. | |
| 5,342,430 A | 8/1994 | Grocela-Kathe et al. | |
| 5,712,405 A | 1/1998 | Nakayama et al. | |
| 5,783,720 A | 7/1998 | Mendicino et al. | |
| 6,465,674 B1 | 10/2002 | Kalchauer et al. | |
| 7,153,991 B2 * | 12/2006 | Lewis et al. | 556/472 |
| 8,637,895 B2 | 1/2014 | Kang et al. | |
| 8,697,901 B2 | 4/2014 | Lewis et al. | |

FOREIGN PATENT DOCUMENTS

| | | | |
|---|---|---|---|
| GB | 1131477 | 10/1968 | |
| WO | 02/44186 A1 | 6/2002 | |
| WO | 2012/080067 A1 | 6/2012 | |
| WO | WO2012080067 | * 6/2012 | ............... C07F 7/16 |

OTHER PUBLICATIONS

International Search Report and Written Opinion mailed Jan. 14, 2015.
Soucek, et al., "Recovering spent contact material in the manufacture of chlorosilances and organochlorosilances", Chem. Abst., vol. 64 (1966) 17638c.
Kopylov, et al., "Recovery of copper from spent cilicon-copper catalyst by hydrometallurgical process", Chem. Abst., vol. 75 (1971) 14421g.
Rathousky, et al., "Direct synthesis of phenylchlorosilanes using the reacted contact material from the direct synthesis of methylchlorosilanes", Chem. Abst. vol. 81 (1974) 78088.
Takami et al., "Catalyst for phenylchlorosilane synthesis", Chem. Abstr., vol. 89 (1978) 509946.
K.M. Lewis et al., "Catalyzed Direct Reactions of Silicon", Elsevier, NY 1993, pp. 28-29.
R.J.H. Voorhoeve, "Organohalosilanes: Precursors to Silicones", Elsevier, Amsterdam 1967, pp. 144-145, 177 & 151-152.
Yeon et al., "Problems and Solutions Involved in Direct Synthesis of Allylchlorosilanes", Organometallics, vol. 12, 1993, pp. 4887-4891.
Petrov et al., "Synthesis of Organosilicon Monomers", Consultants Bureau, New York, 1964, Chapter III, pp. 44-46 & 55.
Forbes et al., "Solvent-Free Cyclization of Linear Dienes Using Olefin Metathesis and the Thorpe-Ingold Effect", J. Am. Chem. Soc., vol. 114 (1992), pp. 10978-10980.
Marvel et al., "The Formation of a Cyclic Recurring Unit in the Polymerization of Diallyldimethylsilane", J. Org. Chem., vol. 25 (Sep. 1960), pp. 1641-1642.
Butler et al., "The Formation of Linear Polymers from Diene Monomers by a Cyclic Polymerization Mechanism, VI. Polymerization Studies of Some Diallylsilanes", J. Org. Chem., vol. 25 (Sep. 1960), pp. 1643-1644.
Vogtle et al., "Multidentate Acyclic Neutral Ligands and their Complexation", Angew. Chem. Int. Ed. Eng., vol. 18, (1979), pp. 753-776.
Debska-Chwaja et al., Soap, Cosmetics and Chemical Specialties; (Nov. 1994), pp. 48-52; ibid., (Mar. 1995), pp. 64-70.
Ramachandran et al., "Three-Phase Catalytic Reactors", Gordon and Breach Science Publishers, New York, 1983.
Gartsman et al., "Mass transfer with chemical reaction in the three-phase system gas-liquid-solid catalyst", International Chemical Engineering, vol. 17, No. 4, (1977), pp. 697-702.
Ying et al., "Gas Holdup in Gas-Liquid-Solid Flow Reactors", Ind. Eng. Chem. Process. Des. Dev., vol. 19, (1980), pp. 635-638.
Satterfield et al., "25 Effects of Mass Transfer on Fischer-Tropsch Synthesis in Slurry Reactors", Chemical Engineering Science, vol. 35, (1980), pp. 195-202.
Boxall et al., "Oxygen Reactor for the Goethite-Zinc Leach Residue Process", Journal of Metals, (Aug. 1984), pp. 58-61.

* cited by examiner

*Primary Examiner* — Sudhakar Katakam
*Assistant Examiner* — Pancham Bakshi
(74) *Attorney, Agent, or Firm* — James C. Abruzzo

(57) ABSTRACT

The present invention is directed to a process for the synthesis of organohalosilane monomers, comprising the steps of (1) forming a slurry of cyclone fines, ultra fines and/or spent contact mass in a thermally stable solvent and reacting the agitated slurry with an organohalide of the formula $R^1X$ in the presence of an additive for a time and at a temperature sufficient to produce organohalosilane monomers having the formulae $R^1SiHX_2$, $R^1{}_2SiHX$, $R^1{}_3SiX$, $R^1SiX_3$, and $R^1{}_2SiX_2$; wherein $R^1$ is a saturated or unsaturated aromatic group, a saturated or unsaturated aliphatic group, alkaryl group, or cycloaliphatic hydrocarbyl group, and X is a halogen; and (2) recovering said organohalosilane monomers.

19 Claims, 4 Drawing Sheets

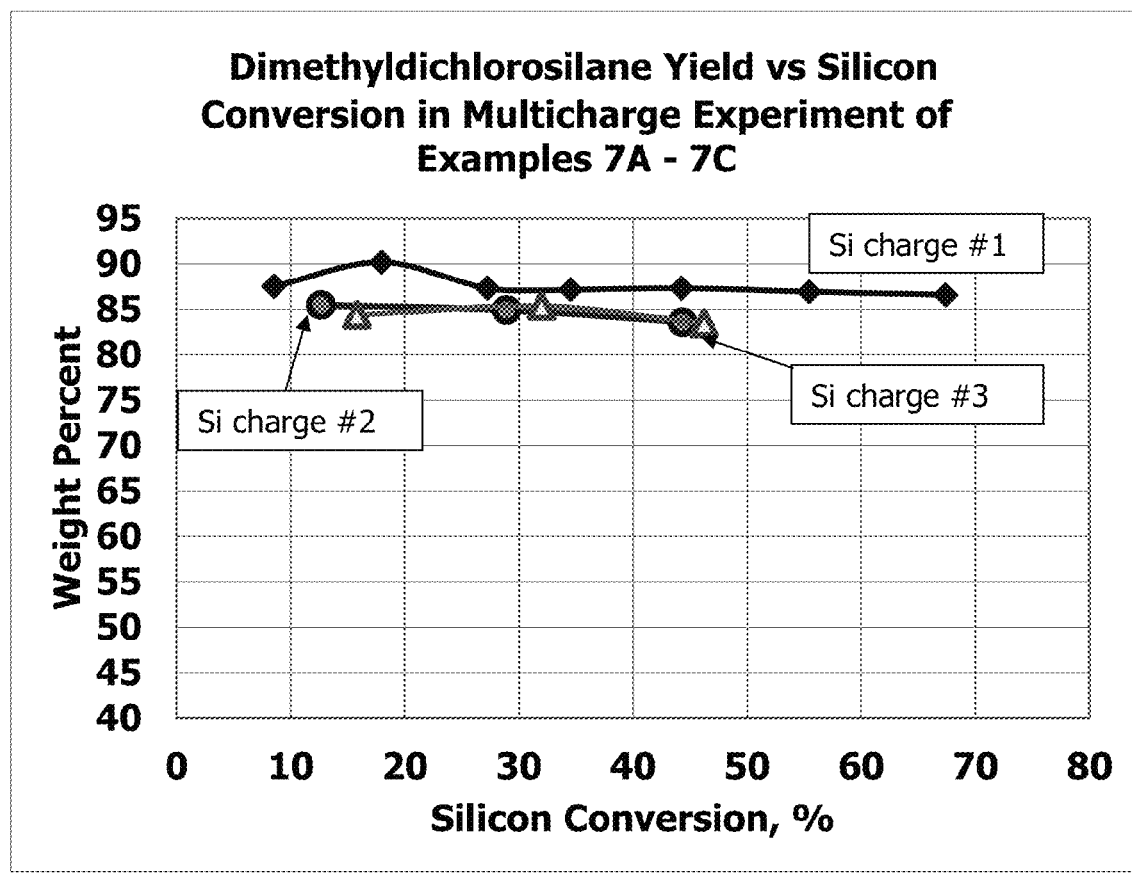
Figure 1(a) (CH$_3$)$_2$SiCl$_2$ Yield in Multicharge Experiment of Examples 7A – 7C

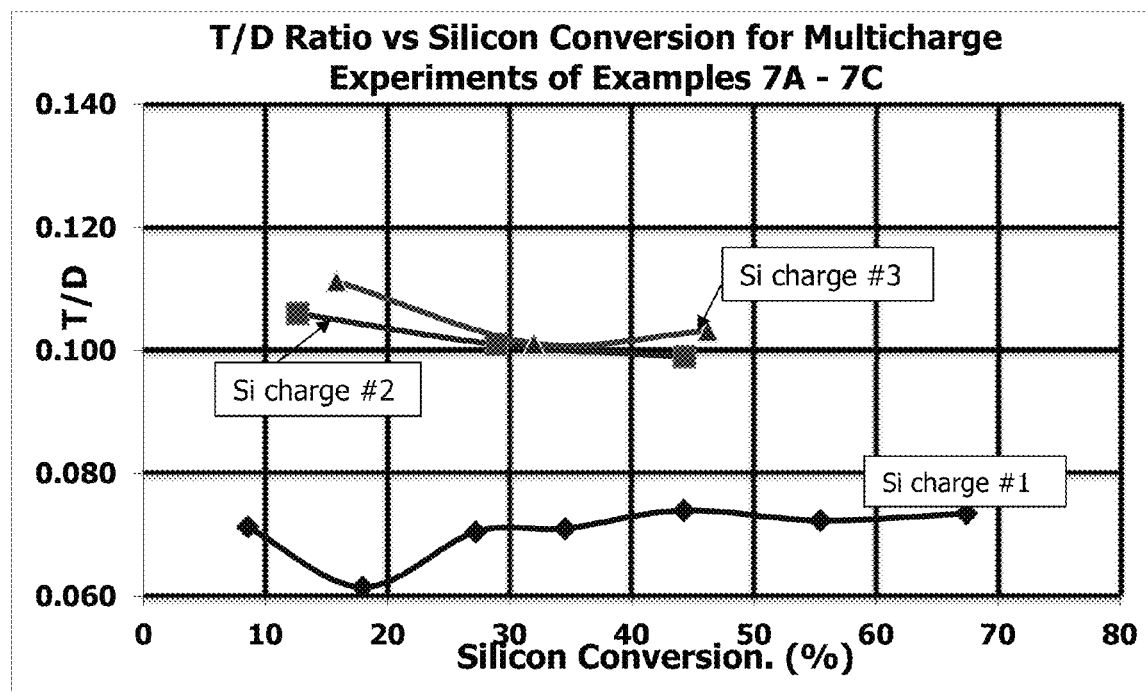
Figure 1(b). T/D Ratios in Multicharge Experiment of Examples 7A – 7C

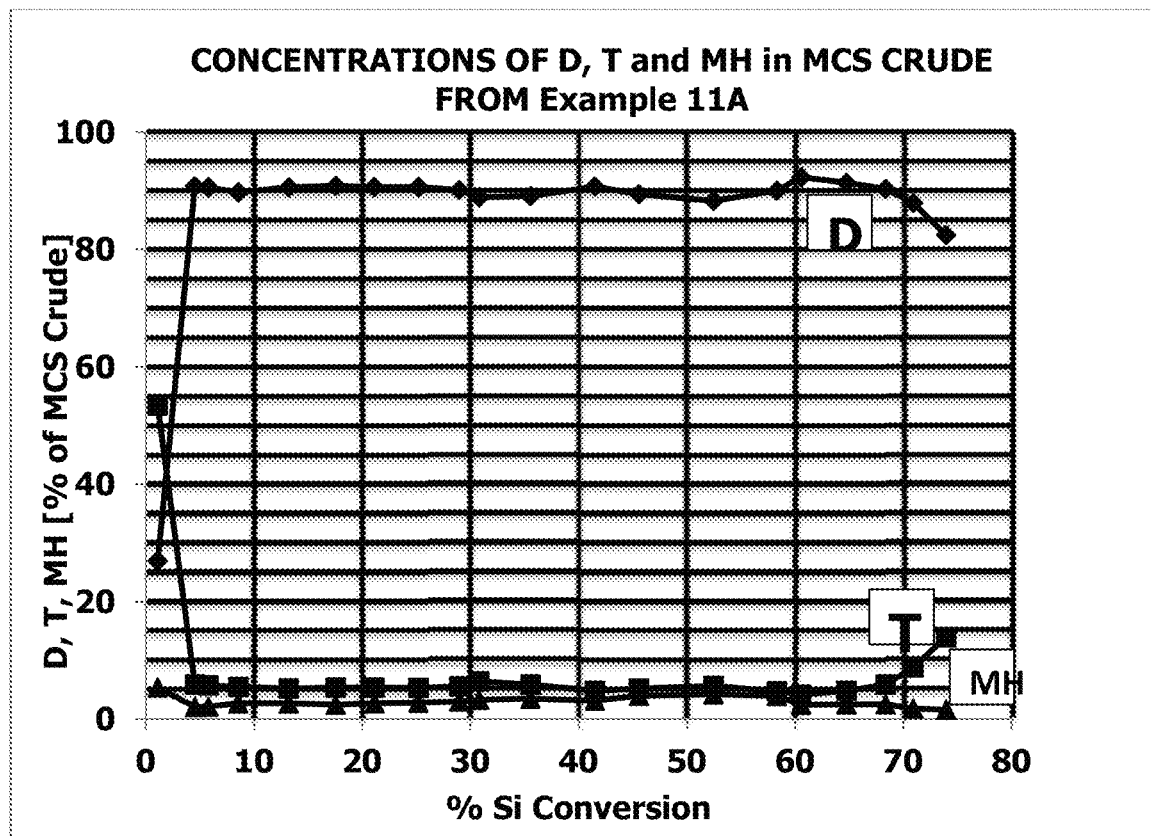
Figure 2. $(CH_3)_2SiCl_2$ (D), $CH_3SiCl_3$ (T) and $CH_3SiHCl_2$ (MH) from Example 11A

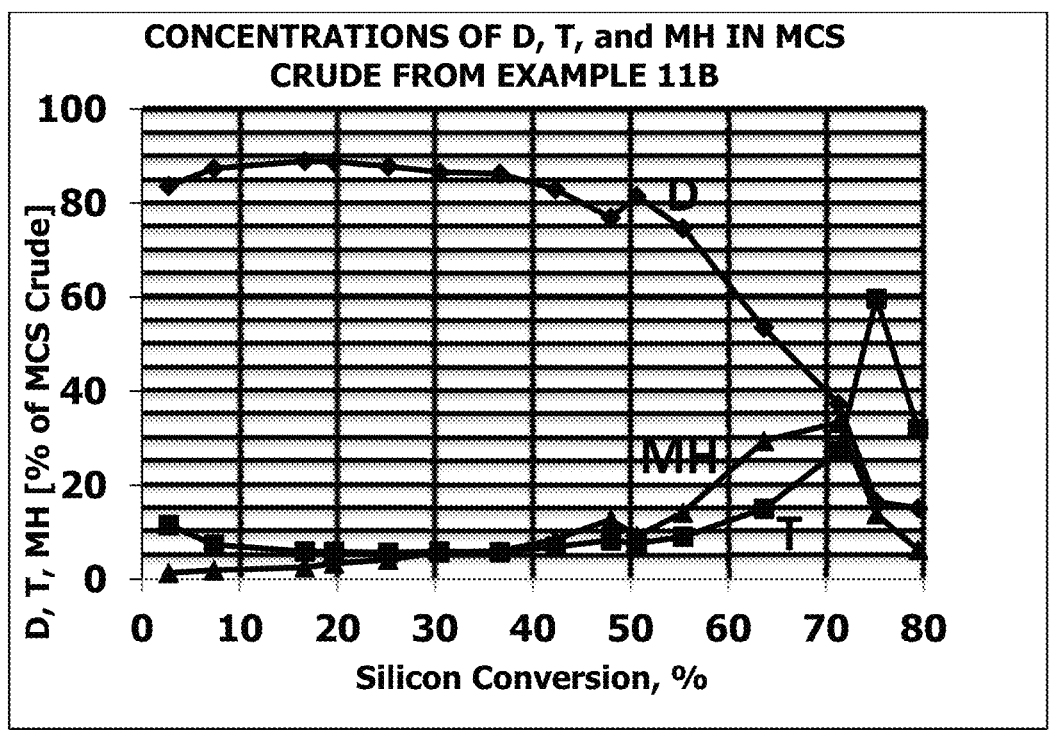
Figure 3. (CH$_3$)$_2$SiCl$_2$ (D), CH$_3$SiCl$_3$ (T) and CH$_3$SiHCl$_2$ (MH) from Example 11B

SLURRY PHASE DIRECT SYNTHESIS OF ORGANOHALOSILANES FROM CYCLONE FINES

This application claims priority to Provisional U.S. Patent Application No. 61/871,962, dated Aug. 30, 2013, the entire contents of which are incorporated herein by reference in their entirety.

FIELD OF THE INVENTION

The present invention discloses the slurry-phase synthesis of organosilane monomers from the silicon-containing solid residues generated during the fluidized-bed Direct Synthesis of organohalosilanes. In particular, this invention discloses the slurry-phase synthesis of organohalosilane monomers from the cyclone-separated or filtered particulates, from the ultra-fine particulates trapped in the condensed crude as well as from the solid wastes retained in the fluidized-bed reactor.

BACKGROUND OF THE INVENTION

Alkylhalosilanes and arylhalosilanes are valuable precursors to silicones and organofunctional silanes that are used in a broad range of industries. Methyl-chlorosilanes and phenylchlorosilanes are particularly valuable and are the most commonly manufactured products of these classes. Manufacture is done using the Rochow-Müller Direct Process (also called Direct Synthesis and Direct Reaction), in which copper-activated silicon is reacted with the corresponding organohalide in a gas-solid or slurry-phase reactor at a temperature and pressure sufficient to effect the desired reaction rate and stability, and product selectivity and yield. Fluidized-bed reactors are the gas-solid reactors most often used. The silicon-containing reaction products are organohalosilanes ($R^1_a SiX_b$), organohalohydrosilanes ($R^1_c SiH_d X_e$), halosilanes ($H_f SiX_g$), organohalodisilanes ($R^1_h NX_j SiSiX_k R^1_l$), organohalopolysilanes ($R^1_m X_q Si—(Si(R^1 X))_n—SiX_q R^1_m$) and carbosilanes ($R^1 X_2 Si—CH_2—SiXR^1_2$, $R^1 X_2 Si—CH_2—CH_2—SiX_2 R^1$ and other similar compounds). Carbosilanes with a single —$CH_2$— group between the silicon atoms are also called silylmethylenes or disilamethanes.

Organohalosilanes have the general formula, $R^1_a SiX_b$, wherein $R^1$ is a saturated or unsaturated aromatic group, a saturated or unsaturated aliphatic group, alkaryl group, or cycloaliphatic hydrocarbyl group such as methyl, ethyl or phenyl, X is a halogen atom such as chlorine or bromine and a and b are positive integers with the proviso that the sum, (a+b)=4.

Organohalohydrosilanes have the general formula, $R^1_c SiH_d X_e$, in which $R^1$ and X have the same meaning as above. The subscripts, c, d and e are positive integers satisfying the sum, (c+d+e=4).

In the halosilanes, ($H_f SiX_g$), f≥0 and g is an integer such that (f+g=4). X is a halogen atom as defined above.

Organohalodisilanes contain one Si—Si bond as indicated in the general formula, ($R^1_h X_j SiSiX_k R^1_l$). $R^1$ and X have the same meanings as defined above. The subscripts, h, j, k and l are individually ≥0 with the sums (h+j=3) and (k+l=3). By extension, trisilanes contain Si—Si—Si units and polysilanes have more than three catenated Si atoms.

Hot effluent exiting from the fluidized-bed reactor, in which copper-activated silicon is undergoing reaction with an organohalide, comprises a mixture of copper, metal halides, silicon, silicides, carbon, gaseous organohalide, organohalosilanes, organohalodisilanes, carbosilanes and hydrocarbons. This mixture is first subjected to gas-solid separation in cyclones and filters (see U.S. Pat. No. 4,328,353). The gaseous mixture and ultrafine solids are condensed in a settler or sludge tank from which the organohalide, organohalosilanes, hydrocarbons and a portion of organohalodisilanes and carbosilanes are evaporated and sent to fractional distillation. The ultrafine solids accumulate in the settler along with the less volatile silicon-containing compounds and this mixture (sludge) is purged periodically and sent to waste disposal or to secondary treatment for the recovery of monomers from the liquid fraction.

Three silicon-containing solid wastes are produced from the fluidized-bed. Elutriated solids, which are trapped by the cyclone or filters, are called cyclone fines or cyclone solids. Those particulates which escape the cyclones and collect in the settler are called ultrafines, settler solids or revaporizer solids. The third category is the solid, which remains unreacted in the fluidized-bed at the end of a campaign. This is called spent mass or spent contact mass. Typically, spent mass has a larger average particle size and wider particle size distribution than cyclone solids and cyclone solids are larger than ultrafines. Spent mass and cyclone fines are dry solids, which can be pyrophoric. Ultrafines are wet and agglomerate into a sludge. For this reason, ultrafines are sometimes called sludge.

A world-class methylchlorosilane plant disposes of thousands of tons of ultrafines, cyclone solids and spent mass per year at considerable cost and loss of raw material values. There are also environmental impacts of the waste disposal methods employed. Accordingly, it is desirable to recover value from these waste solids. Methods of reusing the solids for copper recovery, for production of chlorosilanes, alkoxysilanes, methylchlorosilanes and phenylchlorosilanes have been disclosed in the patent and journal literature.

Passivation of cyclone solids for safe landfill disposal or later recovery of copper is disclosed in U.S. Pat. No. 5,342,430.

U.S. Pat. No. 2,803,521 discloses a method to separate and recover silicon and copper from spent reaction masses. Soucek, et al., (Chem. Abstr. vol. 64 (1966) 17638c) and Kopylov, et al., (Chem. Abstr. vol 75 (1971) 14421g) disclose metallurgical processes for copper recovery from roasted spent masses.

Rathousky, et al. (Chem. Abstr. vol 81(1974) 78008) reported the Direct Synthesis of phenylchlorosilanes using spent mass from the Direct Synthesis of methylchlorosilanes. Takami, et al (Chem. Abstr., vol 89(1978) 509946) disclosed a similar Direct Synthesis of phenylchlorosilanes from methylchlorosilane spent mass that was first heated to 500-900° C.

Ritzer, et al (U.S. Pat. No. 4,390,510) and others have shown that reaction of cyclone fines with HCl produces trichlorosilane and silicon tetrachloride. Reaction with alcohols produces alkoxysilanes. These uses of cyclone solids are cited in *Catalyzed Direct Reactions of Silicon*, K. M Lewis and D. G. Rethwisch (Editors), Elsevier, N.Y. 1993, pages 28-29 and refs cited therein.

U.S. Pat. No. 5,712,405 discloses collection of cyclone fines and filtered fines and recycling them to the bottom of the fluidized bed reactor for further reaction with an organohalide to produce organohalosilanes.

U.S. Pat. No. 6,465,674 discloses introducing cyclone fines into liquid silanes and reinjection of that suspension into the fluidized bed for Direct Synthesis of chloro or organocholorosilanes.

U.S. Pat. No. 4,224,297 discloses a method for the reuse of spent mass with a maximum particle size of 50 microns comprising heating it at 100-350° C. in air or nitrogen for at least 15 hours prior to reacting it with methyl chloride to produce methylchlorosilane monomers.

All of the foregoing references dealing with synthesis of organohalosilanes from cyclone fines and spent mass comprise gas-solid reactions in two phase reactors. Those cited below are all done in three-phase reactors, such as mechanically agitated slurry reactors and bubble columns.

British Patent, GB 1,131,477 claims a process for the preparation of alkylhalo-silanes comprising suspending a contact mass composition in an inert liquid, such as a halogenated aromatic hydrocarbon, at a temperature greater than 175° C. and reacting it with an alkyl halide to produce alkylhalosilanes.

U.S. Pat. No. 7,153,991 discloses the slurry-phase Direct Synthesis of organohalosilanes comprising preparing a slurry of nanosized copper catalyst and silicon, 90 percent of which is between about 1 to about 300 microns, in a thermally stable organic solvent and followed by reaction with an organohalide at temperature greater than 250° C.

Application WO 2012/080067 deals with reaction of finely divided solid residues from the Direct Synthesis of methylchlorosilanes with chloroalkanes in a liquid reaction medium. The finely divided solid residues have silicon content greater than fifty percent and maximum particle size 200 microns, preferably maximally 100 microns. The liquid reaction medium is preferably aprotic and thermally stable. WO 2012/080067 is illustrated with silicon of unspecified particle size that was thermally activated with an unspecified catalyst and promoter(s) to contain catalytically active intermetallic phases. According to WO 2012/080067, this silicon was first suspended in Silicone Oil AP100 (a poly(phenylmethylsiloxane, CAS #63148-58-3)) and reacted with methyl chloride in a stirred autoclave at 3 bar and 350° C. for 110 minutes; solid residue from this reaction was recovered and reacted with methyl chloride, apparently also at 3 bar and 350° C., in a fluidized bed containing Silicone Oil AP100 for 14 minutes; the principal reaction products were dimethyldichlorosilane and trimethylchlorosilane, the former being 2.7 to 4.7 times more than the latter; when the pressure was increased to 10 bar (Example 3), trimethylchlorosilane became the main product, the ratio being 6.1.

In the conclusion to Example 3 of WO2012/080067, it states that "the selectivity to the alkylchlorosilanes can be influenced in a targeted manner via the solubility of methyl chloride in the liquid reaction medium, adjusted by means of the reaction medium and the overpressure, so that trimethylchlorosilane (M3) is the main product of the reaction." It will be shown by examples hereinbelow that trimethylchlorosilane formation in the illustrative experiments of WO 2012/080067 arises from the cleavage of trimethylsilyl groups from Silicone Oil AP100 and is unrelated to the reaction of methyl chloride with the silicon residue.

It is understood by Applicants that WO 2012/080067 states at page 5, line 6 that the disclosed process "constitutes a further direct synthesis" (Application in German, translation into English). In 1967, R. J. H. Voorhoeve (*Organohalosilanes: Precursors to Silicones*, Elsevier, Amsterdam, 1967. Pages 144-145 and ref 177 on page 151) reported that silicone oils and paraffins had been tried as solvents in the slurry-phase Direct Synthesis of organohalosilanes in 1962-1963, but they had been found not to be inert under the reaction conditions. The silicone oils decomposed to give volatile compounds and the paraffins yielded appreciable quantities of tar. The methylchlorosilane reaction product consisted mostly of trichlorosilane and methyltrichlorosilane.

As the foregoing review of the literature shows, there have been many attempts in the past to recover value, particularly methylchlorosilane monomers, from spent mass and cyclone solids produced during the Direct Synthesis of methylchlorosilanes. None of these attempts has resulted in a reliable process that produces a composition of highly valued methylchlorosilanes and methylchlorohydrosilanes.

U.S. Pat. No. 5,338,876 discloses the Direct Synthesis of allylchlorosilanes in stirred-bed and fluidized-bed reactors at 220-350° C. and 1-5 atmospheres, preferably 300-330° C. and 1-3 atmospheres. The disclosure is particularly directed to the Direct Synthesis of allyldichlorosilane by reacting fresh silicon metal with mixtures of allyl chloride and hydrogen chloride, wherein the hydrogen chloride is in molar excess. A companion journal publication with this information is Yeon, et al (*Organometallics*, vol 12 (1993), pp 4887-4891). Other literature references to the Direct Synthesis of allylhalosilanes in fixed, stirred or fluidized bed reactors with fresh silicon metal are the following: *Voorhoeve, Organohalosilanes: Precursors to Silicones*, page 203-204; Petrov, et al., *Synthesis of Organosilicon Monomers*, pp 44-46 and in Table 5, page 55.

Allylhalosilanes are useful intermediates for the synthesis of organic specialties as well as for the synthesis of sulfur-silanes useful in tire and rubber applications. A particularly valuable intermediate is allyltrichlorosilane, which can be converted to allyltriethoxysilane for the synthesis of sulfur-containing silanes.

The polymerization of diallylsubstrates, including diallyldimethylsilane, is reported in the following: Forbes, et al., *J. Amer. Chem. Soc.*, vol 114 (1992) pp 10978-10980; Marvel, et al., *J. Org. Chem.*, vol. 25 (1960) pp 1641-1642; Butler, et al., *J. Org. Chem.*, vol. 25 (1960) pp 1643-1644.

SUMMARY OF THE INVENTION

In one aspect, the present invention is directed to a process for the synthesis of organohalosilane monomers, comprising the steps of (1) forming a slurry of cyclone fines, ultra fines and/or spent contact mass in a thermally stable solvent and reacting the agitated slurry with at least one organohalide of the formula $R^1X$, and optionally organohalosilane and/or hydrogen halide in the presence of an additive for a reaction time and at a temperature and pressure sufficient to produce organohalosilane monomers having the formulae $R^1SiHX_2$, $R^1_2SiHX$, $R^1_3SiX$, $R^1SiX_3$, and $R^1_2SiX_2$ or mixtures thereof; wherein $R^1$ is a saturated or unsaturated aromatic group, a saturated or unsaturated aliphatic group, alkaryl group, or cycloaliphatic hydrocarbyl group, and X is a halogen; and (2) recovering the organohalosilane monomers or mixtures thereof from the solvent.

In another aspect, the present invention is directed to the selective slurry phase Direct Synthesis of allyltrihalosilanes, or mixtures of allyltrihalosilanes and allyldihalosilanes, from cyclone fines and allyl halides, optionally in the presence of hydrogen halides and other additives, via the instant process.

DESCRIPTION OF THE FIGURES

FIG. 1(*a*) is a graph illustrating dimethyldichlorosilane yield vs silicon conversion in multicharge experiments;

FIG. 1(*b*) is a graph illustrating the T/D ratio vs silicon conversion in multicharge experiments;

FIG. 2 is a graph illustrating. $(CH_3)_2SiCl_2$, $CH_3SiCl_3$ and $CH_3SiHCl_2$ concentration vs % Si conversion in Example 11A; and FIG. 3 is a graph illustrating. $(CH_3)_2SiCl_2$, $CH_3SiCl_3$ and $CH_3SiHCl_2$ concentration vs % Si conversion in Example 11B.

DETAILED DESCRIPTION OF THE INVENTION

The present invention is a catalytic process for converting spent mass, cyclone fines and ultrafines from the Direct Synthesis of organohalosilanes into monomers of general formulae, $R^1SiHX_2$, $R^1_2SiHX$, $R^1_2SiX_2$, $R^1_3SiX$ and $R^1SiX_3$, particularly $R^1SiHX_2$, $R^1_2SiHX$ and $R^1_2SiX_2$. $R^1$ and X have the same meanings as has already been defined above. The invention is a three-phase catalytic process, wherein the spent mass, cyclone fines and ultrafines are suspended in a thermally stable liquid and reacted with a gaseous organohalide, in the presence of specific additives and optionally hydrogen halide, at temperatures, pressures, solvent/solid ratios, catalyst concentrations and reaction times sufficient to effect the desired conversion into organohalosilane monomers. This type of three-phase catalytic process is also called a slurry-phase process.

The present slurry-phase process for the Direct Synthesis of organosilane monomers from spent mass, cyclone solids and ultrafines, affords silicon conversion at least 40 weight percent and the ratio, T/(D+MH+M), less than 0.2 when methyl chloride is the reagent organohalide.

The instant catalytic process is also characterized by the use of additives such as diphenylamine, hexamethyldisiloxane, tetra(ethylenegylcol)dimethyl ether, terpenes and triterpenes, which reduce or eliminate the deleterious effects of Lewis acid metal salts and enable both lower solvent/solid ratios and increased silicon conversion to produce the more highly valued organosilane monomers. When the organohalide is a methyl, ethyl or phenyl halide, the more highly valued organosilanes are $R^1_2SiX_2$, $R^1_2SiHX$, $R^1SiHX_2$ and $R^1_3SiX$, wherein $R^1$ is methyl, ethyl or phenyl and X is a halogen. When the organohalide is an allyl halide, the allyltrihalosilane is highly desirable.

Unless defined otherwise, all technical and scientific terms used herein have the same meaning as commonly understood by one of ordinary skill in the art to which this invention belongs. Generally, the nomenclature used herein and the laboratory procedures described are well known and commonly employed in the art. Where a term is provided in the singular, the inventors also contemplate that the plural of that term is also applicable.

By "alkyl" herein is meant to include straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially or deleteriously interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

Podands are acyclic (open-chained) analogs of crown ethers and cryptands. They can be linear or branched as described by F. Vogtle and E. Weber, *Angewandte Chemie, International Edition English*, vol 18., (1979) pp 753-776, which is incorporated herein by reference.

The present invention is a process for the synthesis of organohalosilane monomers of general formulae, $R^1SiHX_2$, $R^1_2SiHX$, $R^1_3SiX$, $R^1SiX_3$ and $R^1_2SiX_2$, or mixtures thereof, by reaction of spent mass, cyclone fines and ultrafines from the fluidized-bed Direct Synthesis of organohalosilanes with an organohalide, $R^1X$, in a three-phase reactor. $R^1$ is an aromatic, aliphatic, alkaryl or cycloaliphatic univalent hydrocarbyl group and X is a halogen atom such as fluorine, chlorine, bromine or iodine. Examples of $R^1$ are methyl, ethyl, phenyl, cyclohexyl, allyl, vinyl and benzyl. The process comprises the following steps: (1) forming a slurry of cyclone fines, ultrafines and/or spent contact mass in a thermally stable liquid in a continuously agitated three-phase catalytic reactor, (2) providing an organohalide to react with the said fines and spent contact mass, (3) introducing specific additives and optional hydrogen halide to enhance selectivity to $R^1SiHX_2$, $R^1_2SiHX$, $R^1_3SiX$ and $R^1_2SiX_2$ and obviate extensive chemical transformation of the thermally stable liquid, (4) reacting said organohalide of formula $R^1X$ and slurry for a time and at a temperature to effectuate conversion of the silicon contained in the fines and contact mass to organohalosilane monomers or mixtures thereof, (5) recovering said monomers or mixtures thereof, (6) separating the solid reaction residue from the liquid and recovering the liquid for reuse in step (1) and passivating the solid for disposal or copper recovery.

It is generally agreed that when $R^1$ is methyl, ethyl or phenyl the organohalosilane monomers of general formula $R^1SiX_3$ are less valuable than those of general formulae, $R^1_2SiX_2$, $R^1_3SiX$, $R^1SiHX_2$ and $R^1_2SiHX$. The slurry-phase process of the instant invention enables the formation of organohalosilane mixtures in which the content of $R^1_2SiX_2$, $R^1_3SiX$, $R^1SiHX_2$ and $R^1_2SiHX$ individually or collectively, exceeds that of $R^1SiX_3$, when $R^1$ is methyl, ethyl or phenyl. The methylchlorosilanes, $(CH_3)_2SiHCl$, $CH_3SiHCl_2$, $(CH_3)_3SiCl$, $(CH_3)_2SiCl_2$ and $CH_3SiCl_3$, are usually abbreviated M2H, MH, M, D and T, respectively. Selectivity to the desired methylchlorosilane composition is defined below.

The preference for diorganodihalosilanes in the Direct Synthesis with saturated organohalides is its selectivity. This is defined as the inverse gravimetric ratio, $R^1SiX_3/R^1_2SiX_2$, abbreviated T/D for methylchlorosilanes. Lower values of this ratio are preferred. T/D values less than 0.2, and preferably less than 0.1, are obtained by the process of the instant invention. Silicon conversions in excess of fifty weight percent, preferably in excess of seventy weight percent, are realized with the present invention.

Another selectivity parameter is the preference for all of the more desirable monomers relative to the organotrichlorosilane. This is calculated as the ratio, $R^1SiX_3/(R^1_2SiX_2+R^1_3SiX+R^1SiHX_2+R^1_2SiHX)$, which for the methylchlorosilanes is T/(D+M+MH+M2H). Values less than 0.2, preferably less than 0.1, are obtained by the process of the instant invention.

Organohalosilanes of general formulae, $R^1SiX_3$ and $R^1SiHX_2$ are desirable and are of higher value when the organohalide is unsaturated and aliphatic as is allyl chloride or allyl bromide. In these cases, the gravimetric ratios, $R^1SiX_3/R^1_2SiX_2$, $(R^1SiHX_2+R^1SiX_3)/R^1_2SiX_2$, $R^1SiX_3/(R^1_2SiX_2+R^1_3SiX+R^1SiHX_2+R^1_2SiHX)$ and $(R^1SiHX_2+R^1SiX_3)/(R^1_2SiX_2+R^1_3SiX+R^1_2SiHX)$ are desirably greater than 1 and preferably greater than 10. One reason for the desirability of $R^1SiX_3$ and $R^1SiHX_2$ is that they can be converted to alkenyl alkoxysilanes, such as allyltriethoxysilane, which have utility as organofunctional coupling agents.

Rate is reported either as the temporal consumption of silicon or organohalide, or as the temporal formation of organohalosilanes. Typical units are weight percent silicon conversion per hour, weight of crude organohalosilanes produced per hour, or kilograms of organohalosilanes per kilogram of silicon per hour. Stability is the maintenance of desirable rate and selectivity until all raw materials are consumed, or consumed beyond a preset silicon conversion.

The organohalide is preferably introduced into the slurry as a gas or vapor. Liquids can be fed provided the flow rate is controlled to avoid large decreases in the reaction temperature and/or rapid expansion of bubbles formed during vaporization. Mixtures of organohalides and mixtures of organohalides with organohalosilanes and/or hydrogen halides can also be used. For example, mixtures of allyl chloride and methyltrichlorosilane or mixtures of allyl chloride and dimethyldichlorosilane can be vaporized and fed to the slurry to forestall thermal decomposition and polymerization of allyl chloride, or polymerization of diallylsilanes, at temperatures greater than about 80° C. Mixtures of allyl halide and hydrogen halide afford increased formation of $R^1SiHX_2$. In the practice of the instant invention, it is required that the molar ratio of allyl halide to hydrogen halide in the feed be greater than or equal to one and preferably greater than 1.5 to obtain balanced formation of both $R^1SiHX_2$ and $R^1SiX_3$.

Spent Contact Mass, Cyclone Fines and Ultrafines

During the Direct Reaction between copper-activated silicon and a gaseous organohalide, silicon is steadily depleted from the contact mass and converted into volatile organohalosilane products. Even with the batchwise or continuous addition of additional silicon, copper catalyst and promoters, a point is reached at which yield and selectivity to the desired products can no longer be sustained economically. Solid residue is left in the reactor at the end of the campaign. This residue is referred to as spent contact mass or spent mass. It comprises unreacted silicon, unreacted copper-activated silicon, copper, copper chlorides and chlorides (e.g., $AlCl_3$, $TiCl_4$, $FeCl_3$) of metals originally present in the silicon, chlorides of the promoter elements (e.g., Zn, Sn, P, Bi) and carbon. Relative to the fresh contact mass, its particle size distribution is depleted in particles less than about 75 microns.

Elutriated solids, which are trapped by the cyclone or filters, are called cyclone fines or cyclone solids. Cyclone solids are usually maximally less than about 50 microns and ninety percent of the particles are between 1.0 and 20 microns. Silicon content is approximately 40-80 weight percent and the contents of Cu, Al, Fe, Sn, Zn, P, C and other elements are enriched compared to fresh or spent contact mass. For example, copper content might be 2 weight percent in spent mass and 10 weight percent in cyclone solids. Aluminum might be about 1 weight percent in spent mass and about 2 weight percent in cyclone solids. Iron might be about 1.5 weight percent in spent mass and about 3 percent in cyclone solids. Tin, zinc and phosphorus can be 5-50 times more concentrated in cyclone solids than in spent mass.

Those particulates, which escape the cyclones and collect in the settler are called ultrafines, settler solids or revaporizer solids. Their particle size ranges from about 0.1 to 5 microns. Silicon content is about 40-60 weight percent, copper about 10-20 weight percent and Al, Fe, Sn, Zn, C and P are usually more concentrated than they are in the cyclone fines and spent mass. While spent mass and cyclone fines are dry solids, which can be pyrophoric, ultrafines are wet with organohalosilanes and agglomerate into a sludge. For this reason, ultrafines are sometimes called sludge.

Sludge can be filtered, centrifuged or dried to separate solids from the liquid. The liquid comprises organohalosilane monomers, organohalodisilanes, organosiloxanes and hydrocarbons. Fractional distillation of the liquid allows recovery of the individual monomers and a disilane fraction, which can be cleaved into monomers by conventional means, as well as by the enhanced methods disclosed in U.S. Pat. Nos. 8,637,895 and 8,697,901, both of which are herein incorporated by reference in their entireties. The solids content of the sludge is advantageously less than 65 weight percent and preferably 20-60 weight percent to facilitate agitation and flow. Sludge can be dried thermally, with or without vacuum, to produce a free flowing powder for use in the present invention. Alternatively, the sludge is added to the reaction solvent, in an amount that permits facile agitation of the resulting slurry, and the organohalosilane monomers, organohalodisilanes, organosiloxanes and hydrocarbons volatilized with heat and inert gas stripping prior to the introduction of the organohalide reactant.

Organohalide

The general formula, $R^1X$, represents the organohalide used to react with the copper-activated silicon of the present invention. $R^1$ is a saturated or unsaturated aliphatic or aromatic hydrocarbon radical and X is a halogen atom. Examples of $R^1$ are groups such as methyl, ethyl, vinyl, allyl and phenyl. Suitable examples of organohalides are methyl chloride, methyl bromide, ethyl chloride, vinyl chloride and chlorobenzene. Methyl chloride and chlorobenzene are the preferred organohalides.

Standard, commercial-grade methyl chloride with a minimum purity of 99.6 weight percent is acceptable as a raw material for the performance of the present Direct Synthesis invention. However, means to remove trace contaminants, or prevent the introduction of volatile inhibitors (for example, CO, $CO_2$, $O_2$, $SO_2$, $H_2O$, $CH_3OH$) of the Direct Synthesis of organohalosilanes could be provided, if desired. For large-scale processes, wherein it is desirable to recycle the unreacted methyl chloride to the slurry reactor, it is advisable to purify the methyl chloride to remove nitrogen and hydrocarbons (for example, methane and isobutane), which might be formed during the Direct Synthesis. They are not themselves poisonous to the formation of methylchlorosilanes, but their presence does decrease the partial pressure of methyl chloride available for reaction.

Chlorobenzene is preferably greater than or equal to ninety-nine weight percent purity for the Direct Synthesis of phenylchlorosilanes. Like methyl chloride, it must not contain any impurities, which can impair the rate, selectivity or stability of the synthesis. Chlorobenzene is best vaporized prior to its injection into the slurry to be reacted.

Allyl chloride is preferably greater than ninety-eight percent purity. It is advantageously vaporized at a temperature less than that which initiates thermal decomposition and polymerization. It can be mixed with hydrogen chloride, methyltrichlorosilane or dimethyldichlorosilane and vaporized at 80-100° C. for injection into the reaction slurry.

Reaction Solvent

Solvents for the Direct Synthesis maintain the particulate solids in a well-dispersed state and facilitate mass transfer of the organohalide to catalytic sites on silicon. The ideal solvents useful in the process of this invention are thermally stable compounds or mixtures that do not degrade under the activation and reaction conditions. Structurally, they are linear and branched paraffins, naphthenes, alkylated benzenes, dialkylated benzenes, aromatic ethers, and polyaromatic hydrocarbons. In the latter, the aromatic rings may be fused together as in naphthalene, phenanthrene, anthracene and fluorene derivatives. They may be joined by single carbon-carbon bonds as in biphenyl and terphenyl derivatives, or they may be joined by bridging alkyl groups, as in the diphenylethanes and tetraphenylbutanes. One class of preferred solvents is the high temperature stable organic solvents typically used as heat exchange media. Examples include THERMINOL® 59, THERMINOL® 60, THERMINOL® 62, THERMINOL® 66, DOWTHERM® HT, DOWTHERM® MX, MARLOTHERM® S, MARLOTHERM® L, MARLOTHERM® LH, diphenyl ether, diphenyl and terphenyl and their alkylated derivatives with normal boiling points higher than about 250° C. THERMINOL® is the Solutia Company trade name for heat transfer fluids. THERMINOL® 59 is a mixture of alkyl-substituted aromatic compounds recommended for use between −45 to 315° C. THERMINOL® 60 is a mixture of polyaromatic compounds with an average molecular weight of 250. Its optimum temperature range is from −45° to 315° C. THERMINOL® 66 and DOWTHERM® HT are mixtures of hydrogenated terphenyls with an average molecular weight of 240. Maximum temperature limit is about 370° C. DOWTHERM® MX and THERMINOL® 62 both contain isomers of diisopropyl biphenyl. DOWTHERM MX is a heat transfer fluid from DOW which is a mixture of alkylated aromatics.

THERMINOL®59, THERMINOL® 62, THERMINOL® 66, DOWTHERM® HT and DOWTHERM® MX are preferred solvents of this invention. DOWTHERM® fluids are produced by Dow Chemical Company. DOWTHERM® MX and THERMINOL® 62 are preferred solvents for the instant invention. MARLOTHERM® is the Sasol trade name for its heat transfer fluids. MARLOTHERM® S is a mixture of isomeric dibenzylbenzenes. MARLOTHERM® L and MARLOTHERM® LH are mixtures of isomeric benzyl toluenes. All three of these MARLOTHERM fluids can be used at temperatures up to about 350° C.

Suitable alkylated benzenes for the practice of the instant Direct Process are dodecylbenzene, tridecylbenzene, tetradecylbenzene and their mixtures such as are sold by Vista Chemical Company under the trade name NALKYLENE®, and by Condea Augusta s.p.a. under the trade names ISORCHEM® and SIRENE®. NALKYLENE® 550BL, NALKYLENE® 550L, NALKYLENE® 500, NALKYLENE® 501 and NALKYLENE® 600L are suitable reaction solvents for use in the present invention. NALKYLENE® V-7050 is comprised of dialkylated benzenes with initial boiling point greater than 320° C. It is a particularly preferred reaction solvent for the present invention.

Naphthenes are cycloparaffins. They are components of white mineral oils, petroleum distillates and some fuels. White mineral oils and petroleum distillates also contain normal and branched paraffins (see A. Debska-Chwaja, et al., *Soap, Cosmetics and Chemical Specialties*, (November 1994), pp 48-52; ibid., (Mar. 1995) pp 64-70). Suitable examples of commercial products containing naphthenes and paraffins and useful as reaction solvents for this invention are the white mineral oils, CARNATION 70, KAYDOL, LP-100 and LP-350, and the petroleum distillates, PD-23, PD-25 and PD-28, all of which are sold by Crompton Corporation under the Witco trade mark. Other examples of naphthenes useful as reaction solvents are decahydronaphthalene, perhydroanthracene, perhydrophenanthrene, perhydrofluorene and their alkylated derivatives, perhydroterphenyl, perhydrobinaphthyl and their alkylated derivatives. CALFLO™ Heat Transfer Fluids sold by Petro-Canada are paraffinic materials that are thermally stable up to about 250-330° C. Suitable examples are CALFLO™ LT, CALFLO™ AF and CALFLO™ HTF. Calflo-LT is a heat transfer fluid which is a mixture of synthetic and restructured hydrocarbons in combination with patented oxidation inhibitors. CALFLO LT is recommended for heat transfer systems that require high thermal efficiency over a wide temperature range from −40° C. to 260° C. (−40° F. to 500° F.). CALflo-AF is an efficient heat transfer fluid designed for use in systems operating continuously at temperatures up to 316° C. (600° F.), CALFLO AF is a blend of pure HT hydrocracked base oils and a proprietary Petro-Canada additive system.

Squalane is another paraffinic solvent suitable for the instant slurry-phase Direct Synthesis process. Its unsaturated derivative, squalene, is also an effective solvent. Direct Syntheses with the paraffin and olefinic solvents are desirably conducted at temperatures less than 330° C. Mixtures of alkylated benzenes, naphthenes and normal and branched paraffins and alkenes with polyaromatic hydrocarbons are also useful as reaction solvents for the instant invention.

It is desirable that all solvents be free of components with normal boiling points less than 200° C. and, in particular, compounds which have normal boiling points that overlap with those of the organohalosilanes to be produced. It is also advantageous for the practice of this invention that the solvent does not degrade into lower molecular weight compounds when it is heated alone, or in contact with cyclone fines, ultrafines and sludge at temperatures up to about 350° C. and pressures up to about 10 bar. Product distillation and refining can be complicated by lower molecular weight hydrocarbons and other compounds with normal boiling points which overlap those of the organohalosilanes. It is desirable that formation of these impurities be avoided or prevented. However, limited alkylation of the solvent to produce higher molecular weight compounds is permissible when the organohalide is introduced. Limited oxidative coupling of aromatic moieties is also permissible.

Used solvents can be treated for removal of solids, metal salts, disilanes and other accumulated impurities, prior to recycle and reuse in the slurry reactor. Remediation comprises filtration of solids and stripping of the filtrate at temperatures up to about 250° C. (atmospheric pressure) to remove lower boiling hydrocarbons, disilanes and siloxanes. Alternatively, the solvent can be recovered by distillation in vacuo to separate it from the copper-laden solids destined for copper recovery.

Cyclone fines, ultrafines and/or spent mass and solvent can be added together in the reactor in any order. The solvent is present in an amount sufficient to disperse the solid and gaseous reactants homogeneously. Generally, reactions are initiated with solvent and solids in a gravimetric ratio between 1:2 and 6:1, preferably 2:1 to 5:1. However, as the silicon is consumed during batchwise Direct Synthesis, the solvent to solids ratio will increase. The ratio can be maintained within narrow limits of the preferred range for continuous reactions.

Additives

The presence of Lewis acids such as $AlCl_3$, $TiCl_4$ and $FeCl_3$ and of free copper in cyclone fines, ultrafines and spent mass contributes to organohalide cracking, solvent transformation and other side reactions, which either do not produce organohalosilanes, or produce those of lesser value such as those of general formula, $R^1SiX_3$, when $R^1$ is a saturated aliphatic group, an aromatic group, an alkaryl group, or a cycloaliphatic hydrocarbyl group. These undesirable reactions can be inhibited or controlled by the use of selected additives, which, among other mechanisms, can coordinate or react with the Lewis acids or adsorb on free copper surfaces. The Lewis acids and free copper referred to include both what are present in the initial cyclone fines, ultrafines and spent mass feed materials and what are generated as a result of the Direct Synthesis with organohalides in the reaction slurry. The additives must not inhibit the Direct Synthesis, or induce unwanted chemical reactions in the organohalosilanes being produced.

Polyethers, including podands, bind $AlCl_3$ and other Lewis acids and make them ineffective at interfering in the desired Direct Synthesis of organohalosilanes. Alpha-omega dialkylpolyethers, such as penta(ethyleneglycol)dimethyl ether, tetra(ethyleneglycol)dimethyl ether, tri(ethyleneglycol)dimethyl ether and dibenzo(triethyleneglycol)dimethyl ether, are effective additives. Secondary amines, such as diphenylamine, with boiling points greater than about 250° C. are a second class of suitable additives. Organosiloxanes such as polydimethylsiloxanes such as the non-limiting example of hexamethyldisiloxane are another class. Terpenes, including turpentine and triterpenes such as squalene, are a fourth class. Nitrohydrocarbons such as nitrobenzene are a fifth class. Trivinylcyclohexane is also effective as are nitriles such as adiponitrile and 1,6-dicyanohexane.

The high-boiling secondary amines can be added at the outset of a reaction or at any time during the reaction. Usage must be sufficient to enable effective inactivation of the competitive pathways such as organohalide cracking, solvent transformation and undesirably high $R^1SiX_3$ formation. Usage of 0.05-10 weight percent, optimally 2-5 weight percent, based on the weight of silicon-containing particles charged to the reaction slurry, is effective.

Organosiloxanes with trialkylsilyl endgroups, particularly hexaalkyldisiloxanes, are effective additives that permit stable slurry-phase Direct Synthesis of organohalosilanes from cyclone fines, ultrafines and spent masses. Trimethylsilyl-endblocked polydimethylsiloxanes with viscosities up to 1000 centistokes are also effective additives. Most effective are those with viscosities in the range 5-100 centistokes. Usage of the hexaalkyldisiloxanes, for example, hexamethyldisiloxane, can be based on the aluminum content of the silicon-containing solids to be reacted. Owing to the high volatility hexamethyldisiloxane, its effective molar ratio usage relative to aluminum is in the broad range, 0.5 to 10, and preferably 1 to 5. With polydimethylsiloxanes, the mass ratio relative to aluminum is broadly 5 to 50 and preferably 10 to 30.

Terpenes, diterpenes and triterpenes are effective at reducing or eliminating decomposition of the solvents and contributing to stable slurry-phase Direct Synthesis of organohalosilanes from cyclone fines, ultrafines and spent masses. Pinene. limonene and squalene are suitable examples. Those, like squalene or pinene, that form solid or non-volatile complexes with aluminum halides and other Lewis acids contained in the fines are preferred. Effective use levels can be determined by the aluminum content of the fines. Amounts that are 0.05-5 times the number of moles of aluminum are effective when added at the outset of a reaction or at any time during the reaction.

Compounds containing the cyano or nitrile (CN) functionality are effective additives for the slurry-phase Direct Synthesis process of this invention. One representative class comprises organonitriles, preferably those with normal boiling points higher than the temperature at which the Direct Synthesis is conducted. Mono-functional nitriles of this invention have the general formula, RCN, in which R is an aliphatic group of eleven or more carbon atoms, or cycloaliphatic, aryl, or alkaryl group containing more than six carbon atoms. Examples include the nitriles, $CH_3(CH_2)$—CN, n=10-17.

In the formula, RCN, R can also contain functional groups, which will not interfere with the conduct of the desired organohalosilane Direct Synthesis. Thus, R can contain ether (—C—O—C—) groups. Suitable examples are cyanoalkyl ethers of general formula, $RO(CH_2)$—CN and [CN$(CH_2CH_2)_y]_2O$, wherein y is an integer from 1 to 20, preferably 1 to 4.

Difunctional, trifunctional and other multifunctional nitriles are also effective additives of reaction stability during the slurry-phase Direct Synthesis of organohalosilanes from cyclone fines and spent contact masses. Difunctional organonitriles have two cyano groups per molecule. These may be on the same carbon atom, as for example in malonitrile, $CH_2(CN)_2$, and 1,1-dicyano-cyclohexane, or on different carbon atoms as in 1,2-dicyanobenzene, α,ω-dicyanoalkanes and 1,4-dicyanocyclohexane. The α,ω-dicyanoalkanes are especially preferred. They have general formula, $CN(CH_2)_xCN$, in which x is an integer greater than or equal to one. Preferred additives of this formula comprise those with x=4-9.

The trifunctional organonitriles have three cyano groups per molecule. These can be on the same carbon atom as in $R"C(CN)_3$, in which R" is hydrogen, an aliphatic, cycloalpihatic, aryl, or alkaryl group, or on different carbon atoms as in 2,4,6-tricyanotoluene and the variously substituted isomeric tricyanoalkanes.

In the context of this invention, compounds with four or more cyano groups per molecule are termed multifunctional. They comprise aliphatic compounds like 1,1,2,2-tetracyanoethane, aromatic compounds like 1,2,4,5-tetracyanobenzene, and cycloaliphatic compounds like 2,2,3,3-tetracyanoethylene oxide.

Use levels of the mono, di and multifunctional nitriles can be determined from the aluminum content of the cyclone fines and spent mass. The stoichiometric ratio, (CN/Al), can be 0.05-3 at the outset of a reaction or at any time during the reaction.

In all cases, the additives are charged initially and dosed continuously or intermittently, thereafter, during the course of the reaction. The initial charge and subsequent dosage must be effective to afford stable selectivity to the desired silane (dimethyldichlorosilane when the organohalide is methyl chloride and allyltrichlorosilane when the organohalide is allyl chloride) and forestall solvent decomposition.

Reaction Conditions,

Designs, descriptions and operational considerations pertinent to three-phase reactors (for example, agitated slurry reactors, bubble columns, trickle beds) are contained in the following monograph, articles and patents, all of which are incorporated by reference herein:

A. Ramachandran and R. V. Chaudhari, *Three Phase Catalytic Reactors*, Gordon and Breach Science Publishers, NY, 1983.

N. Gartsman, et al., *International Chemical Engineering*, vol. 17 (1977) pp 697-702

H. Ying, et al., *Industrial & Engineering Chemistry, Process Design & Development,* vol. 19 (1980) pp 635-638

N. Satterfield, et al., *Chemical Engineering Science, vol.* 35 (1980) pp 195-202

M. Boxall, et al., *Journal of Metals*, (August 1984) pp 58-61

W. Roeckel, C. Scaccia and J. Conti, U.S. Pat. No. 4,328,175 (May 4, 1982)

L. M. Litz, U.S. Pat. No. 4,454,077 (Jun. 12, 1984)

Reactors may be operated in a batchwise or continuous mode. In batchwise operation, a single addition of cyclone fines, ultrafines or spent mass, individually or admixed with each other, is made to the reactor at the outset and organohalide is added continuously, or intermittently, until the silicon is fully reacted, or reacted to a desired degree of conversion.

In continuous operation, cyclone fines, ultrafines and/or spent mass, and optionally additives, are added to the reactor initially and thereafter to maintain the solids content and composition of the slurry within desired limits.

In its preferred form in accordance with the present invention, the Direct Synthesis of organohalosilanes from the silicon-containing particulate solid residues of the Direct Process is conducted in a continuously agitated slurry reactor containing solvent, cyclone fines, ultrafines and/or spent mass, additives and foam control agents in contact with gaseous organohalide. The reactor may have a single nozzle or multiple nozzles for the introduction of gas. A means of continuous or intermittent addition of cyclone fines, ultrafines or spent mass and additives is also provided. Means for continuous removal and recovery of the volatile reaction products and unreacted organohalide are also desirably provided. Separation and purification of the organohalosilane products are optimally performed by continuous fractional distillation as described, for example, for methylchlorosilanes in *Soviet Chemical Industry* (*English Translation*), (1970), pp 70-75; (1985), pp 294-300.

The reaction is generally conducted at temperatures above about 180° C., but below such a temperature as would degrade or decompose the reactants, solvents or desired products. Preferably, reaction of methyl chloride, methyl bromide, ethyl chloride or chlorobenzene with ultrafines, cyclone fines and spent masses is conducted in a range from about 230° C. to about 450° C. The reaction of methyl chloride with the cyclone fines, ultrafines or spent mass of the present invention is preferably operated at 240-350° C., whereas the reaction of chlorobenzene is preferably operated at 300-450° C. Reaction of allyl chloride with the cyclone fines, ultrafines or spent masses is preferably done at 200-280° C. The pressure at which the reaction is conducted can be varied from subatmospheric to superatmospheric. Atmospheric pressure and pressures up to about 10 atmospheres are generally employed. The preferred range is 1 to 5 atmospheres. Reaction times ranges from 0.1 to 100 hours.

Preferably, the contents of the reaction mixture are agitated to maintain a well-mixed slurry of the cyclone fines, ultrafines or spent mass and gaseous organohalide in the solvent. Agitation speed and power must be sufficient to keep the largest particles suspended in the solvent, and not settled on the bottom of the reactor.

The exit line carrying the reaction mixture from the reactor is preferably well insulated to insure that the organohalosilanes remain gaseous. Solvent vapors and droplets present in the gas stream can be removed by cooling to temperatures that are still above the boiling points of the organohalosilanes, and/or by passing the reaction mixture through a demister. Volatile metal salts such as $AlCl_3$, $FeCl_2$, $SnCl_2$, $TiCl_4$, $ZnCl_2$ and mixed metal salts (for example, $CuAlCl_4$) that escape the slurry can also be removed thereby.

The presence of gaseous organohalide, organohalosilanes and other gases in the reactor can occasionally lead to foaming. This is undesirable since it can result in loss of solvent and solids from the reactor. U.S. Pat. No. 5,783,720 (1998) discloses that the addition of foam control agents, preferably silicon-containing foam control agents such as Momentive products, SAG® 1000, SAG® 100, SAG® 47, and FF170 and Dow Corning FS 1265, will negate or control foaming in the slurry phase Direct Synthesis of trialkoxysilanes. They are also effective foam control agents in the process of the instant invention. SAG® 1000, SAG® 100 and SAG®47 are compositions comprising polydimethylsilicones and silica. FS 1265 and FF170 contain fluorinated silicones, for example, poly(dimethylsiloxane-co-trifluoropropyl-methylsiloxanes).

The foam control agent is preferably durable such that a single addition at the outset of a batch reaction is sufficient to avoid or mitigate foam formation until all of the silicon has been consumed. Physical and mechanical methods of preventing or controlling foam formation can also be employed. These include rakes, ultrasonic devices, and foam arrestors.

EXAMPLES

The following Examples illustrate the preferred embodiments of the instant invention. They are not intended to limit the scope of the invention. Rather, they are presented to facilitate experimental verification of the invention by those of ordinary skill in the art.

TABLE 1

Abbreviations and Units Used

| ABBREVIATION | MEANING | ABBREVIATION | MEANING |
|---|---|---|---|
| g | Gram | D | $(CH_3)_2SiCl_2$ |
| kg | Kilogram | T | $CH_3SiCl_3$ |
| cm | Centimeter | M | $(CH_3)_3SiCl$ |
| $m^2/g$ | square meters per gram | MH | $CH_3SiHCl_2$ |
| h | Hour | TC | $HSiCl_3$ |
| nm | Nanometer | % Si/h | weight percent silicon converted per hour |
| μ | Micrometer | cSt | Centistokes |
| wt % | weight percent | ppm | parts per million |

Equipment Used for Illustrative Examples

A 2.0 liter glass reactor (Reactor A) was used for some of the experiments presented in the illustrative Examples. Agitation was provided by two pitched, glass blades attached to an axial shaft, which was also of glass. The bottom blade was 5.7 cm in diameter and the top 3.9 cm. The blades were separated by 3.8 cm. A Caframo BDC 1850 Stirrer with digital speed control was the power source for agitation. An electric heating mantle controlled by a digital heater/temperature was used to heat the reactor.

Methyl chloride was supplied to the reactor from a cylinder via a calibrated flowmeter. The gas was preheated to 100° C. by transit through a 30 cm long×0.32 cm diameter coiled, stainless steel tube placed in a silicone oil bath. Stainless steel tubing from the oil bath to the reactor inlet was also controlled at 100° C. with an electrical heating tape.

Chlorobenzene was supplied to the reactor from a 1 liter reservoir via a calibrated FMI pump. The oil bath (described above) and transfer lines were controlled at 160° C. to keep the chlorobenzene (normal boiling point 137° C.) gaseous.

Allyl chloride used was a commercial product of 98.5-99.5% purity. Principal impurities comprised 2-chloropropene, 2-chloropropane, 1-chloro-1-propene, and 1,5-hexadiene In some experiments, it was delivered into the top of the reaction slurry by syringe. In others, it was vaporized at 80° C. and introduced at the bottom of the reactor. Mixtures of allyl chloride with methylchlorosilanes or HCl were also used in some experiments.

Reaction products and unreacted organohalide exited the reactor through a foam arrestor and a 40 cm long×2.5 cm diameter Vigreux column controlled at 140-160° C. when methyl chloride was the organohalide. This served as an entrainment separator for solvent droplets and metal salts. The gaseous reaction mixture was then admitted to a condenser, cooled to ~0° C. with chilled silicone oil, before it was collected in a sampling flask attached to a dry ice-isopropanol cold finger. Gas leaving the collection flask was cooled in second dry ice-isopropanol cold finger before being vented to the hood through a vapor lock bubbler. The bubbler contained silicone oil and had an extra opening for the release of overpressure.

Samples were collected in flat-bottomed flasks and set aside for evaporation of unreacted methyl chloride prior to gas chromatographic analysis. The evaporation step was not necessary with chlorobenzene reactions.

Gas chromatographic analysis of the reaction product was performed on a HP 5890E chromatograph. The column was 10 ft×¼inch i.d. packed with 30 wt % OV-210 on acid washed Chrom P. Programs, flow rates and other conditions were appropriate for the samples analyzed (see *Catalyzed Direct Reactions of Silicon*, loc. cit., Chapters 8 and 9).

Gas Chromatography/Mass Spectrometry (GC/MS) analyses were carried out with an Agilent 6890GC/5973 MSD instrument fitted with a 30 meter-long ZB5 (5% phenyl, 95% methylpolysiloxane) capillary column. Column inner diameter was 0.25 mm and film thickness was 2.5 µm. The carrier gas was helium with 200:1 injection split ratio. The injection port and GC/MS interface temperatures were 250° C. and 270° C., respectively. Injection volume was 1 ul. The oven temperature was held at 50° C. for 2 minutes before it was raised at a rate of 8° C./min to 340° C., and then was held for 16 minutes. The mass spectrometer was operated in the EI (70 eV electron impact ionization) full scan (m/z 10-800) mode.

For NMR characterization, samples were analyzed with a Bruker AVANCE 600 Spectrometer operating at field strength of 14.1 T. Protons ($^1$H's) resonate at 600 MHz at this field strength. Samples for $^{29}$Si nmr were prepared as a 25% to 30% by volume solution in $Cr(AcAc)_3/CDCl_3$ to a final Cr salt concentration of ~0.05M $Cr(AcAc)_3$. The solution was placed in a 10 mm NMR tube. Chemical shifts were externally referenced to tetramethylsilane (TMS). An inverse gated decoupling pulse sequence was used with a pulse width of 45-degrees for $^{29}$Si. A delay of 10 s was used between scans (AQ of 1.4 s). The data were processed using a LB of 2 Hz.

Reactor B was assembled from a 1 Liter resin flask and cover with four 24/40 ports. The flask was heated with a temperature-controlled heating mantle. A PTFE gasket was positioned between the cover and flask to enable safe, leak-proof closure with clamps. A mechanical agitator, a gas inlet tube, a product outlet line, and a thermowell containing a thermocouple, which was connected to the heating mantle controller, were attached to the reactor cover. The gas inlet tube extended below the agitator. Gases, methyl chloride and nitrogen, were delivered to the reactor through separate calibrated flowmeters. The gas lines were connected with a "tee" so that they could be fed separately or mixed. A 12.7 cm long (5 inch) column packed with 0.95 cm (⅜ inch) glass helices was the product outlet. It was connected to a condenser/receiver cooled with −22° C. liquid from a circulating chiller. All lines carrying the refrigerated coolant were heavily insulated. One of the 24/40 ports contained an agitator and another, a thermowell with a thermocouple connected to the thermocontroller.

A 10.5 Liter stainless steel reactor (Reactor C) was used for reactions undertaken at greater than ambient pressure. The reactor mixing system was designed so that different agitators could be installed based on the needs of the process. The agitator shaft had a flange joint enabling the different bottom shafts sections to be quickly changed. This allowed studies to be done with a variety of impellers or mixers ranging from an anchor style agitator that is normally used at low rotational speeds to a variety of Rushton and hydrofoil impellers normally used at high rotational speeds. One high speed impeller design that was used consisted of a pair of impellers. The lower was a Rushton type 76 mm in diameter while the upper impeller was a hydrofoil type 86 mm in diameter. The centerline spacing between the impellers was 81 mm. The reactor also had two interchangeable speed reduction gears and motor with a variable frequency drive controller that allowed operations from 4 to over 500 rpm. When baffles were needed, a 14.3 cm diameter by 16.5 cm long removable 4-baffle assembly was installed in the reactor. The baffles were 1.27 cm wide and were 0.4 cm away from the reactor wall.

Temperature was controlled with a heat transfer oil circulator equipped with digital PID temperature controller capable of either electrically heating the oil or cooling it indirectly with water circulating through an external heat exchanger. The reactor was also equipped with electric heat tracing with separate zone controllers to maintain reactor or vapor column metal temperature. Pressure was maintained by a conventional control loop consisting of a pressure transmitter mounted on the reactor with an output to a digital PID control that automatically adjusted the opening of a backpressure control valve.

Methyl chloride gas was supplied to the reactor from a cylinder via a calibrated Brooks® mF™ series mass flow controller. The gas was introduced into the reactor through stainless steel tubing through nozzles in the reactor at either the side or the bottom after passing through a small orifice or a porous metal filter element. Nitrogen was supplied from a cylinder via a separate flow meter.

Reaction products and unreacted organohalide exited the reactor through an insulated and electrically traced line and packed column with 30 cm of 6.1 mm Pro-Pak® protruded stainless steel column packing. This column served as the entrainment separator for solvent droplets and metal salts. The gaseous mixture was admitted to a condenser cooled with circulating water/ethylene glycol to less than −20° C. or to a greater temperature as would be appropriate for the greater operating pressure. The condensed liquid was collected in a stainless steel receiver from which samples were obtained for analysis and mass balance.

Gas chromatographic analysis of the reaction product was performed using an Aligent model 7890A or model 6850 chromatograph. A Restex RTX-200, 105 meter, 0.32 mm ID capillary column was used.

A Parr 300 ml stirred autoclave (Reactor D) was used for the experiments summarized in comparative Examples 1A-1D.

Materials Used for Illustrative Examples

Cyclone fines and ultrafines (sludge) were obtained from commercial production of methylchlorosilanes. Solvents included the methyl phenyl silicone oil AP100, Calflo™ AF, Calflo™ LT, Therminol® 62, FDA-22™, Marlotherm® LH, Dowtherm® MX, and Nalkylene® V-7050.

FDA-22 is provided by Royal Purple, Ltd and it is a proprietary synthetic based oil with isoparrafinic diluents.

Methyl chloride and allyl chloride were standard commercial products.

Comparative Examples 1A-1D

The following experiments were conducted in Silicone Oil AP100 as taught in WO 2012/080067. These experiments are designed to show that the formation of trimethylchlorosilane derives from the Silicone Oil AP100 and is independent of the reaction of cyclone fines, or any other solid silicon-containing Direct Process residue, with methyl chloride.

Each experiment in Examples 1A, 1B and 1C was done in Reactor D at 350° C. with the weights of cyclone fines, Silicone Oil AP100 and the quantities of methyl chloride, $CH_3SiCl_3$ and $SiCl_4$ shown in Table 2, along with the quantitative gc analyses of the reaction mixtures. Example 1D was done with Calflo™ AF as the solvent. All compounds in the reaction mixtures were positively identified by gc/ms.

TABLE 2

DATA FOR COMPARATIVE EXAMPLES 1A-1D

| | COMPARATIVE EXAMPLE 1A | COMPARATIVE EXAMPLE 1B | COMPARATIVE EXAMPLE 1C | COMPARATIVE EXAMPLE 1D |
|---|---|---|---|---|
| Cyclone Fines, g | 5.0 | 5.2 | 7.5 | 5.2 |
| Silicone AP 100, g | 100.7 | 100.5 | 100.4 | 103.0 |
| $CH_3Cl$, mole | 0.03 | | | 0.03 |
| $CH_3SiCl_3$, g | | 3.2 | | |
| $SiCl_4$, g | | | 10.6 | |
| PRODUCT COMPOSITION | | | | |
| $(CH_3)_3SiCl$, wt % | 49 | 36 | 79 | |
| $CH_3SiCl_3$, wt % | | | | |
| $(CH_3)_2SiCl_2$, wt % | 8 | | 2 | |
| Benzene, wt % | 22 | 40 | 10 | |
| $(CH_3)_3SiOSi(CH_3)_3$, wt % | 10 | 19 | 3 | |
| $SiCl_4$, wt % | | | | >85 |

The data show that $(CH_3)_3SiCl$ was formed in the experiments of Comparative Examples 1B and 1C, wherein $CH_3Cl$ was not included. Accordingly, $(CH_3)_3SiCl$ formation was unrelated to the reaction of $CH_3Cl$ with silicon contained in the cyclone fines. Additionally, since no $CH_3$ or $(CH_3)_3Si$ groups were introduced in the experiment of Comparative Example 1C (with $SiCl_4$), the source of $(CH_3)_3SiCl$, $(CH_3)_3SiOSi(CH_3)_3$ and benzene had to Silicone Oil AP100, whose structure is shown below.

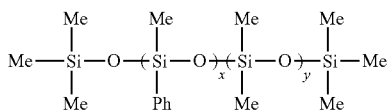

where Me=$CH_3$, Ph=$C_6H_5$, x=9.35, y=5.28

Examples 2A-2C

Examples 2A-2C illustrate the reactivity in the temperature range, 260-300° C., of ultrafines (sludge) with methyl chloride to produce methylchlorosilane monomers. All three reactions were done with Therminol® 62 in the 2 liter glass reactor (Reactor A) described hereinabove. Sludge used in Examples 2A and 2B was from the same sample. That for Example 2C was taken from a different source at a different time. Prior to reaction with methyl chloride, sludge was stripped of its contained methylchlorosilanes by heating it to 200° C., in a 4-necked round bottom flask, and simultaneously sparging with dry nitrogen and stirring mechanically. The evolved material was condensed in a cold trap. The sticky solid retained in the flask was later transferred to the 2 liter glass reactor.

TABLE 3

SUMMARY OF EXAMPLE 2A
Materials and Conditions: Therminol ® 62, 1050 g;
Sludge, 500 g; $CH_3Cl$, 150 ml/min; Defoamer FF170,
4 g; Agitation, 500 rpm; Temperature, 260-285° C.

| SAMPLE | TEMP° C. | REACTION TIME, h | SAMPLE WEIGHT, g | T/D |
|---|---|---|---|---|
| 1* | 260 | | 18 | 1.86 |
| 2 | 260-280 | 1.67 | 44 | 1.19 |
| 3 | 285 | 2.67 | 40 | 0.98 |

*$CH_3Cl$ introduced after Sample 1 when there was no further condensation of methylchlorosilanes originally present in the sludge.

TABLE 4

SUMMARY OF EXAMPLE 2B
Materials and Conditions: Therminol ® 62, 1022 g;
Sludge, 570 g; $CH_3Cl$, 150 ml/min; Defoamer FF170,
4 g; Agitation, 500 rpm; Temperature, 300° C.

| SAMPLE | TEMP° C. | REACTION TIME, h | SAMPLE WEIGHT, g | T/D |
|---|---|---|---|---|
| 1* | 300 | | 20 | 1.86 |
| 2 | 300 | 1.0 | 89 | 1.18 |
| 3 | 300 | 2.0 | 80.5 | 1.20 |
| 4 | 300 | 3.0 | 40 | 1.72 |

*$CH_3Cl$ introduced after Sample 1 when there was no further condensation of methylchlorosilanes originally present in the sludge.

TABLE 5

SUMMARY OF EXAMPLE 2C
Materials and Conditions: Therminol ® 62, 908.4 g;
Sludge, 587.4 g; $CH_3Cl$, 150 ml/min; Defoamer FF170,
4 g; Agitation, 500 rpm; Temperature, 280° C.

| SAMPLE | TEMP° C. | REACTION TIME, h | SAMPLE WEIGHT, g | T/D |
|---|---|---|---|---|
| 1* | | | 58.8 | 0.77 |
| 2 | 280 | 1.0 | 64.7 | 1.77 |
| 3 | 280 | 2.2 | 117.4 | 2.14 |
| 4 | 280 | 3.7 | 28.8 | 3.50 |

*$CH_3Cl$ introduced after Sample 1 when there was no further condensation of methylchlorosilanes originally present in the sludge.

The data of Tables 3-5 show that the ultrafine silicon and copper-activated silicon particles contained in the sludge reacted with methyl chloride in a slurry reactor to produce methylchlorosilane compositions that were different from, and often of lower T/D ratio than, the original sludge liquid.

Example 3A-3G

These Examples illustrate the slurry phase reaction of methyl chloride and cyclone fines in aliphatic and aromatic solvents. All reactions were done in Reactor A with cyclone fines whose composition and particle size distribution are summarized in Table 6.

TABLE 6

COMPOSITION AND PARTICLE SIZE DISTRIBUTION OF CYCLONE FINES
(Particle size range 1-10 μM, Mean 5 μm)

| Cu, wt % | Al, wt % | Ca, ppm | Fe, wt % | P, ppm | Ni, ppm | Sn, ppm | Zn, ppm |
|---|---|---|---|---|---|---|---|
| 8-10 | 1.2-1.5 | 4500-5000 | 3.0-3.5 | 150-220 | 130-1500 | 50-100 | 5000-8000 |

The results (Tables 7 and 8) show that the Direct Synthesis was successful both in the aliphatic and aromatic solvents. Reaction performance (measured as T/D, D wt % and Si Conversion) was better in FDA-22™, Calflo™ AF, Nalkylene® V-7050, Dowtherm® MX and Therminol™ 62 than in Calflo™ LT and Marlotherm® LH. Formation of low molecular weight hydrocarbons with boiling points overlapping the methylchlorosilane range was observed in the experiments with FDA-22™ and Calflo™ LT. These hydrocarbons (C3-C6) were not present in the fresh solvent and so probably arose from cracking of longer aliphatic chains. GC/MS analysis of the post-reaction solvents showed evidence of higher molecular weight hydrocarbons (normal boiling points >100° C.) in the experiments with FDA-22™, Dowtherm® MX, Therminol™ 62 and Marlotherm® LH.

TABLE 7

METHYLCHLOROSILANE DIRECT SYNTHESIS IN
ALIPHATIC AND AROMATIC SOLVENTS
(CH$_3$Cl Flow 0.5 L/min, Agitation 500 rpm)

| EX | SOLVENT | TEMP, ° C. | RATIO* | TIME, h | CONV % | T/D |
|---|---|---|---|---|---|---|
| 3A | FDA-22 ™ | 295 | 3 | 20.5 | 75 | 0.07 |
| 3B | Calflo ™ LT | 280 | 3 | 5.0 | 14 | 0.05 |
| 3C | Calflo ™ AF | 300 | 5 | 15.0 | 70 | 0.11 |
| 3D | Marlotherm ® LH$^a$ | 275 | 3 | 2.0 | low | 0.06 |
| 3E | Dowtherm ® MX | 295 | 3 | 15.5 | 75 | 0.09 |
| 3F | Therminol ™ 62 | 295 | 3 | 14.5 | 63 | 0.10 |
| 3G | Nalkylene ® V-7050$^a$ | 300 | 3 | 10.0 | 65 | 0.07 |

*RATIO = Initial Solvent/Solids gravimetric ratio, a = 0.8 L/min

TABLE 8

COMPOSITION OF METHYLCHLOROSILANE PRODUCTS
FROM THE EXPERIMENTS OF EXAMPLES 3A-3G

| EXAMPLE | Si CONV, % | MH, wt % | M, wt % | T, wt % | D, wt % |
|---|---|---|---|---|---|
| 3A | 75 | 4.0 | 1.3 | 5.8 | 84.4 |
| 3B | 14 | 1.2 | 0.8 | 4.9 | 88.9 |
| 3C | 70 | 1.4 | 1.1 | 10.1 | 86.5 |
| 3D | Low | Trace | 0.1 | 0.8 | 14.1 |
| 3E | 75 | 4.0 | 1.1 | 7.3 | 86.8 |
| 3F | 63 | 3.3 | 0.8 | 6.4 | 88.6 |
| 3G | 65 | 1.3 | 1.3 | 6.2 | 88.6 |

The data of Table 8 show that cyclone fines can be reacted with methyl chloride under slurry-phase conditions in selected aliphatic and aromatic solvents to produce 84-89 wt % dimethyldichlorosilane and 1-4 wt % methyldichlorosilane. Silicon conversion was 63-75%. In other experiments, silicon conversions reached 80-85% and dimethyldichlorosilane remained >80 wt %.

Examples 4A-4H

The nine experiments of these Examples illustrate the effects of methyl chloride flow rate, reaction temperature, stirring speed and solvent to solid ratio on the performance parameters of slurry-phase Direct Synthesis of methylchlorosilanes from cyclone fines in the solvent, Calflo™ AF. The performance parameters monitored were T/D, T/(D+MH), D wt % and Si conversion.

All reactions were run in Reactor A with cyclone fines whose composition and particle size distribution are disclosed in Table 6. Reaction times were 6-12 hours. Unless otherwise stated, the experimental results summarized in Table 9 are for measurements up to the six hour mark.

TABLE 9

EFFECT OF REACTION TEMPERATURE, CH$_3$Cl FLOW RATE,
SOLVENT/SOLID RATIO AND AGITATION SPEED ON SLURRY PHASE DIRECT
SYNTHESIS OF METHYLCHLOROSILANES IN CALFLO ™ AF.

| EX | TEMP ° C. | CH$_3$Cl (L/min) | RATIO* | AGITATION (RPM) | T/D | T/(D + MH) | Si Conv wt % |
|---|---|---|---|---|---|---|---|
| 4A | 300 | 0.8 | 2 | 350 | 0.144 | 0.129 | 32.2 |
| 4B | 270 | 0.55 | 3.5 | 500 | 0.063 | 0.063 | 16.9 |
| 4C | 240 | 0.8 | 5 | 650 | 0.22 (2 h) | 0.22 (2 h) | 1.4 (2 h) |
| 4D | 300 | 0.3 | 2 | 350 | 0.12 | 0.11 | 14.2 |
| 4E | 300 | 0.3 | 2 | 650 | 0.093 | 0.091 | 19.8 |
| 4F | 300 | 0.8 | 2 | 650 | 0.129 | 0.118 | 31.0 |
| 4H | 300 | 0.8 | 5 | 350 | 0.073 | 0.070 | 39.6 |
| 4J | 300 | 0.3 | 5 | 650 | 0.059 | 0.058 | 26.7 |
| 4K | 300 | 0.3 | 5 | 350 | 0.071 | 0.070 | 25.1 |

*RATIO = Initial Solvent/Solids gravimetric ratio

The data from Examples 4A, 4F and 4H show that higher $CH_3Cl$ flow rate and higher temperature yielded faster reaction rates. The reaction was considerably slower at 240° C. (Example 4C). Initial solvent/solids ratio had a major impact on the selectivity (T/D) to dimethyldichlorosilane. Larger solvent/solids ratios (greater than 2: Examples 4B, 4C, 4H, 4J and 4K) afforded higher selectivity to dimethyldichlorosilane (lower T/D). The agitation speed in the range tested appears to have minimum impact on either the reaction rate or the selectivity of the products. However, the reaction rates were decreased tremendously in the two runs with 70 and 150 rpm, respectively. It is likely that with such mild agitation the solids were not fully in suspension and/or that there was insufficient power to provide effective mass transfer of $CH_3Cl$ gas to the liquid phase and then to the solid phase for reaction.

Example 5A-5H

These Examples illustrate the effect of initial solvent/solids gravimetric ratio on silicon conversion and T/D during the slurry-phase Direct Synthesis of methylchlorosilanes from cyclone fines in Calflo™ AF, Therminol™ 62 and Dowtherm® MX. All reactions were done in Reactor A with the cyclone fines described in Table 6. Experimental data are summarized in Table 10.

TABLE 10

EFFECT OF INITIAL SOLVENT/SOLIDS RATIO ON STABILITY OF SLURRY PHASE DIRECT SYNTHESIS OF METHYLCHLOROSILANES FROM CYCLONE SOLIDS

| EXAMPLE | SOLVENT | TEMP, C. | RATIO | Si CONV, T/D < 0.1 | D, wt % |
|---|---|---|---|---|---|
| 5A | Calflo™ AF | 300 | 5 | 58 | 90.4 |
| 5B | Calflo™ AF | 300 | 4 | 43 | 85.0 |
| 5C | Calflo™ AF | 300 | 1.58 | 12 | 85.6 |
| 5D | Dowtherm ®MX | 295 | 4 | 70 | 87.2 |
| 5E | Dowtherm ®MX | 295 | 3 | 67 | 86.6 |
| 5F | Therminol™ 62 | 295 | 3 | 63 | 88.7 |
| 5G | Therminol™ 62 | 295 | 2 | 30* | 23.2 |

*T/D = 0.7

The criterion of acceptable performance in these experiments is catalytic stability. That is the duration (silicon conversion) of the Direct Synthesis while maintaining good selectivity (T/D<0.1 and dimethyldichlorosilane>80 wt %). The data of Table 10 are consistent in showing that, for each of the three solvents studied, higher initial solvent/solid gravimetric ratios afford higher silicon conversions and higher selectivity to dimethyldichlorosilane.

Example 6

This Example illustrates reuse of solvent, previously used in the slurry-phase Direct Synthesis of methylchlorosilanes from cyclone fines, in a subsequent Direct Synthesis. The reused solvent was Calflo™ AF recovered from the reaction residue of Example 5A.

Used Calflo™ AF was treated with water and the mixture stirred for ~1 hour. It was then pressure filtered to remove the solids. The filtrate was heated to 100° C. under nitrogen sparging to remove water. 527 g of remediated Calflo™ AF was recovered in this way. It was mixed with 262 g fresh Calflo™ AF and used in the reaction of 157.8 g cyclone fines in Reactor A at 300° C. with 0.8 L/min methyl chloride. Reaction was continued for 12 hours (70% silicon conversion). Data for samples taken at 8 hours and 12 hours are summarized in Table 11.

TABLE 11

SLURRY-PHASE DIRECT SYNTHESIS OF METHYLCHLOROSILANES WITH RECOVERED Calflo ™ AF

|  | 49% Si CONVERSION | 70% Si CONVERSION |
|---|---|---|
| TIME, h | 8 | 12 |
| $(CH_3)_2SiHCl$, % | 0.3 | 0.9 |
| $CH_3SiHCl_2$, % | 1.6 | 2.9 |
| $(CH_3)_3SiCl$, % | 1.0 | 3.6 |
| $CH_3SiCl_3$, % | 9.8 | 18.7 |
| $(CH_3)_2SiCl_2$, % | 85.8 | 72.8 |
| T/D | 0.11 | 0.26 |

The data clearly show that slurry-phase Direct Synthesis of methylchlorosilanes with cyclone fines was sustained in a solvent comprising previously used Calflo™ AF.

Example 7A-7C

This Example illustrates the reuse of a single charge of solvent with more than one charge of cyclone fines without first recovering and/or remediating the solvent. This practice is called multi-charging.

The experiments were conducted in Reactor A at 295° C. with Dowtherm® MX and initial solvent to solids ratio of 3:1 in Example 7A. After about 67% silicon conversion, 133 g additional cyclone fines (Example 7B) were added to the reactor and reaction continued with methyl chloride until about 44% conversion of this second charge of cyclone fines. A third charge of 100.73 g cyclone fines (Example 7C) was made at that point and reaction again continued to about 46% silicon conversion. The data are summarized in Tables 12, 13, 14 and 15 and in FIG. 1.

TABLE 12

EXPERIMENTAL DATA ILLUSTRATING REACTION OF THREE SILICON CHARGES ON A SINGLE CHARGE OF DOWTHERM ® MX

| VALUE | EXAMPLE 7A | EXAMPLE 7B | EXAMPLE 7C |
|---|---|---|---|
| Cyclone Fines, g | 276 | 190 | 143.90 |
| Silicon $^a$, g | 193.2 | 195.98$^b$ | 209.87$^c$ |
| Defoamer FF170, g | 3.9 | None Added | None Added |
| Dowtherm ® MX, g | 828 | None Added | None Added |
| $CH_3Cl$, L/min | 0.8 (5 hours), 0.5 (10 hours) | 0.8 (5 hours), 0.5 (3 hours) | 0.8 (5 hours), 0.5 (3.5 hours) |
| Agitation, rpm | 500 | 500 | 500 |
| Temperature, ° C. | 295 | 295 | 295 |
| Total Reaction Time, h | 15 | 8 | 8.50 |
| Product Composition |  |  |  |
| MCS Crude, g | 634.60 | 427.90 | 467.60 |
| $(CH_3)_2SiHCl$, % | 0.61 | 0.63 | 0.57 |
| $CH_3SiHCl_2$, % | 4.01 | 5.39 | 4.40 |
| $(CH_3)_3SiCl$, % | 1.10 | 1.30 | 1.34 |
| $CH_3SiCl_3$, % | 6.18 | 8.53 | 8.89 |
| $(CH_3)_2SiCl_2$, % | 87.73 | 83.90 | 84.45 |
| HVS, % | 0.17 | 0.13 | 0.19 |
| Total Hydrocarbons % | 0.20 | 0.12 | 0.16 |
| T/D | 0.07 | 0.10 | 0.10 |

TABLE 12-continued

EXPERIMENTAL DATA ILLUSTRATING REACTION
OF THREE SILICON CHARGES ON A SINGLE CHARGE
OF DOWTHERM ® MX

| VALUE | EXAMPLE 7A | EXAMPLE 7B | EXAMPLE 7C |
|---|---|---|---|
| Si Conversion, % | 67.76 | 44.31 | 46.21 |
| Average Rate, % Si Conversion/h | 4.52 | 5.54 | 5.44 |

[a] Fines contained 70% Si.

[b] Includes 62.98 g Si from Example 7A reaction

[c] Includes 109.14 g Si from Example 7B reaction

Overall 609.90 g cyclone fines, which contained 426.93 g silicon, were reacted in three charges on a single charge of 828 g solvent (Dowtherm® MX). Thus, the cumulative solvent/solids ratio was 1.36. A total of 1455 g methylchlorosilane crude with T/D 0.093 and containing 85.35 wt % D and 4.39 wt % MH was produced over 31.5 hours. Final silicon conversion was 73.7% and methyl chloride conversion was 40%.

TABLE 13

TIME COURSE OF $(CH_3)_2SiCl_2$ AND
$CH_3SiHCl_2$ FORMATION AND T/D AND T/(D +
MH) IN THE EXPERIMENT OF EXAMPLE 7A.

| TIME, h | Si CONV, % | MH, wt % | D, wt % | T/D | T/(D + MH) |
|---|---|---|---|---|---|
| 2.00 | 8.52 | 3.79 | 87.53 | 0.071 | 0.068 |
| 4.00 | 17.93 | 1.53 | 90.18 | 0.062 | 0.060 |
| 6.00 | 27.22 | 3.51 | 87.33 | 0.071 | 0.068 |
| 7.50 | 34.52 | 3.95 | 87.15 | 0.071 | 0.068 |
| 10.00 | 44.24 | 4.10 | 87.32 | 0.074 | 0.071 |
| 12.50 | 55.42 | 4.46 | 86.94 | 0.072 | 0.069 |
| 15.00 | 67.40 | 4.57 | 86.59 | 0.073 | 0.070 |

TABLE 14

TIME COURSE OF $(CH_3)_2SiCl_2$ AND
$CH_3SiHCl_2$ FORMATION AND T/D AND T/(D +
MH) IN THE EXPERIMENT OF EXAMPLE 7B.

| TIME, h | Si CONV, % | MH, wt % | D, wt % | T/D | T/(D + MH) |
|---|---|---|---|---|---|
| 2.50 | 12.63 | 3.38 | 85.47 | 0.106 | 0.101 |
| 5.50 | 28.89 | 3.90 | 84.92 | 0.101 | 0.096 |
| 8.00 | 44.31 | 5.18 | 83.58 | 0.099 | 0.093 |

TABLE 15

TIME COURSE OF $(CH_3)_2SiCl_2$ AND
$CH_3SiHCl_2$ FORMATION AND T/D AND T/(D +
MH) IN THE EXPERIMENT OF EXAMPLE 7C.

| TIME, h | Si CONV, % | MH, wt % | D, wt % | T/D | T/(D + MH) |
|---|---|---|---|---|---|
| 3.00 | 15.80 | 3.83 | 84.39 | 0.111 | 0.106 |
| 6.00 | 31.98 | 3.65 | 85.36 | 0.101 | 0.097 |
| 8.50 | 46.21 | 5.26 | 83.44 | 0.103 | 0.097 |

Examples 8A-8B

These Examples illustrate the use of multi-charging with the aliphatic solvent, FDA-22™

Two reactions were conducted in Reactor A following the method described above in Example 7. In the first (Example 8A), 355.1 g cyclone fines were charged to 1060 g FDA-22™ and 230.9 g in the second (Example 8B). The second addition of cyclone fines was made after 68.39 percent of the initially charged silicon had been converted to methylchlorosilanes. The second charge was reacted for 17.3 hours during which silicon conversion reached 60.97 percent. Additional experimental conditions and results are summarized in Table 16.

The data show that selectivity to $(CH_3)_2SiCl_2$ was ~80% during the first charge and (T/D) was ~0.09. In the second charge, $(CH_3)_2SiCl_2$ decreased to 74-80% and $CH_3SiCl_3$ increased from ~7% to 8-10%. Accordingly, (T/D) increased to 0.11-0.14. However, overall valuable monomer (M+MH+D) formation was consistently 83-88% during the 37.8 hours of both experiments.

TABLE 16

EXPERIMENTAL DATA ILLUSTRATING REACTION OF TWO SILICON
CHARGES ON A SINGLE CHARGE OF FDA-22 ™

| VALUE | EXAMPLE 8A | | | EXAMPLE 8B | |
|---|---|---|---|---|---|
| Cyclone Fines, g | 355.1 | | | 230.9 | |
| Silicon [a], g | 248.57 | | | 240.2 [b] (161.63 + 78.57) | |
| Defoamer FF170, g | 4.4 | | | None added | |
| FDA-22, g | 1060 | | | None added | |
| $CH_3Cl$, L/min | 0.5 | | | 0.5 | |
| Agitation, rpm | 500 | | | 500 | |
| Temperature, ° C. | 295 | | | 295 | |
| Total Reaction Time, h | 20.5 | | | 17.3 | |
| Total MCS Crude, g | 851.20 | | | 828.50 | |

| | FIRST CHARGE | | | SECOND CHARGE | |
|---|---|---|---|---|---|
| Reaction Time, h | 6.00 | 14.50 | 20.5 | 7.50 | 15.00 |
| MCS Crude, g | 253.50 | 326.50 | 271.20 | 407.70 | 367.80 |
| $(CH_3)_2SiHCl$, % | 0.96 | 0.81 | 0.86 | 0.78 | 0.98 |
| $CH_3SiHCl_2$, % | 3.98 | 6.04 | 6.65 | 6.29 | 10.46 |
| $SiCl_4$, % | 1.16 | 0.85 | 0.70 | 0.55 | 0.75 |
| $(CH_3)_3SiCl$, % | 1.31 | 1.24 | 1.36 | 1.51 | 1.67 |
| $CH_3SiCl_3$, % | 7.07 | 6.93 | 6.95 | 8.81 | 10.08 |

TABLE 16-continued

EXPERIMENTAL DATA ILLUSTRATING REACTION OF TWO SILICON
CHARGES ON A SINGLE CHARGE OF FDA-22 ™

| VALUE | EXAMPLE 8A | | | EXAMPLE 8B | |
|---|---|---|---|---|---|
| $(CH_3)_2SiCl_2$, % | 79.69 | 80.27 | 81.11 | 79.70 | 74.17 |
| HVS, % | 0.00 | 0.00 | 0.00 | 0 | 0 |
| Total Hydrocarbons % | 5.60 | 3.70 | 2.24 | 2.26 | 1.81 |
| T/D | 0.089 | 0.086 | 0.086 | 0.111 | 0.136 |
| Si Conversion, % | 20.06 | 46.30 | 68.39 | 16.01 | 55.75 |
| Average Rate, % Si/h | 3.34 | 3.19 | 3.33 | 2.13 | 3.71 |

Example 9A-9B

These Examples illustrate the use of tetraethylene glycol dimethylether (also called Tetraglyme) to reduce solvent decomposition (hydrocarbon formation) and maintain good selectivity to $(CH_3)_2SiCl_2$ during the Direct Synthesis of methylchlorosilanes from cyclone fines in the aliphatic solvent, Calflo™ LT.

Two identical Reactor B units were operated simultaneously. Both reactors used methyl chloride from the same cylinder. One reactor was used as a control (Example 9A), while the other (Example 9B) was fitted with a syringe pump, which was connected to the methyl chloride feed line such that a liquid additive could be continually fed into the reactor during the experiment.

Each reactor was charged with 452 g of Calflo™ LT oil, 0.9 g of SAG-47 antifoam and 141 g of the same batch of cyclone fines, which contained 1.3 wt % aluminum and 75% silicon. The reactors were heated to 300° C. under nitrogen and agitated at 445 rpm. The syringe pump was charged with tetraglyme (tetraethyleneoxide dimethylether), and the pump was started at a rate of 0.5 ml/hr just before the start of methyl chloride feed to the reactor of Example 9B. Methyl chloride was fed at 450 ml/min to both reactors and this rate was maintained throughout the run. Condensate appeared in both reactors almost immediately after methyl chloride feed began, and samples were taken hourly for analysis by GC. After 5 hours of run time, the tetraglyme rate in Example 9B was increased to 1.02 ml/hr. and was maintained at this rate until the reactions were terminated, which was 20 hours for both reactors. The data are summarized in Tables 17 and 18.

At termination, silicon conversion in the control experiment (Example 9A) was ~64 percent and ~73 percent in the tetraglyme-promoted experiment (Example 9B). So the average rate was 1.14 times greater in the experiment with tetraglyme addition than in the control. Table 17 shows that dimethyldichlorosilane (D) content in the hourly samples of Example 9A followed a decreasing trend between 5 and 64 percent silicon conversion. A steady-state was never established. Moreover, T/D increased beyond 0.1 after about 25 percent silicon conversion and reached ~0.4 at 49 percent silicon conversion. In contrast, aside from the first sample (0.5 h), T/D remained at or below 0.1 until 66 percent silicon conversion in Example 9B (see Table 18). Dimethyldichlorosilane (D) content in the hourly samples remained at 84-88 percent between 3 and 66 percent silicon conversion. A stable steady-state was established. It is clear that the continuous addition of tetraglyme improved the rate, selectivity and stability of the slurry-phase Direct Synthesis of methylchlorosilanes from cyclone fines.

In the control (Example 9A), methyldichlorosilane (MH) formation increased from 5 to 28 percent between 20 and 54 percent silicon conversion. With the addition of tetraglyme (Example 9B), MH remained less than 3 percent throughout the experiment.

Hydrocarbons are generated as a result of the decomposition of Calflo™ LT. This decomposition is probably catalyzed by $AlCl_3$ and other Lewis acids present in the reaction slurry. Paraffinic and olefinic hydrocarbons with six and fewer carbon atoms overlap the boiling range of the methylchlorosilane monomers and are likely to contaminate these compounds during fractional distillation. Hydrocarbons with normal boiling points greater than about 75° C. are also formed, or might have been volatilized from the Calflo™ LT solvent. Total hydrocarbon formation (HC) recorded in column 9 of Tables 17 and 18 is the sum of all hydrocarbons generated in the product samples, irrespective of their boiling points.

In the control (Example 9A, Table 17), total hydrocarbons fluctuated between 1-7 percent up to 54 percent silicon conversion. A rapid increase to 14-26 percent occurred thereafter. Most of this increase was attributable to hydrocarbons with normal boiling points lower than about 75° C. The ratio of these lower boiling hydrocarbons to those boiling greater than 75° C. increased from 0.73 to about 2.01 at silicon conversion greater than 58 percent.

TABLE 17

DATA FOR EXAMPLE 9A: REACTION WITHOUT TETRAGLYME

| Time, h | Sample Weight, g | M2H, % | MH, % | Siltet, % | M, % | T, % | D, % | HC, % | HVS, % | T/D | Si Conv., % |
|---|---|---|---|---|---|---|---|---|---|---|---|
| 1.00 | 14.60 | 0.45 | 0.91 | 0.80 | 0.87 | 9.54 | 81.40 | 5.07 | 3.66 | 0.117 | 2.24 |
| 2.00 | 18.51 | 0.51 | 1.06 | 0.61 | 0.76 | 5.04 | 86.80 | 4.20 | 2.74 | 0.058 | 5.04 |
| 3.00 | 22.85 | 0.40 | 1.28 | 0.67 | 0.64 | 4.97 | 86.71 | 4.29 | 2.41 | 0.057 | 8.51 |
| 4.00 | 23.63 | 0.43 | 1.81 | 0.58 | 0.60 | 5.80 | 84.42 | 5.20 | 2.69 | 0.069 | 12.12 |
| 5.00 | 20.70 | 0.51 | 4.38 | 0.59 | 0.58 | 6.66 | 79.59 | 6.62 | 2.62 | 0.084 | 15.38 |
| 6.00 | 22.97 | 0.57 | 3.53 | 0.63 | 0.67 | 7.33 | 84.57 | 2.20 | 2.00 | 0.087 | 18.82 |
| 7.00 | 16.58 | 0.79 | 4.99 | 0.57 | 0.78 | 7.66 | 82.93 | 1.91 | 1.85 | 0.092 | 21.51 |
| 8.00 | 19.82 | 1.07 | 6.47 | 0.63 | 0.83 | 8.04 | 80.58 | 1.97 | 1.83 | 0.100 | 24.61 |
| 9.00 | 21.15 | 1.24 | 8.75 | 0.39 | 0.85 | 8.41 | 71.70 | 1.70 | 1.44 | 0.117 | 28.15 |
| 10.00 | 22.36 | 1.52 | 12.36 | 0.52 | 0.99 | 9.98 | 72.61 | 1.64 | 1.50 | 0.137 | 31.66 |

TABLE 17-continued

DATA FOR EXAMPLE 9A: REACTION WITHOUT TETRAGLYME

| Time, h | Sample Weight, g | M2H, % | MH, % | Siltet, % | M, % | T, % | D, % | HC, % | HVS, % | T/D | Si Conv., % |
|---|---|---|---|---|---|---|---|---|---|---|---|
| 11.00 | 24.00 | 1.65 | 15.75 | 0.67 | 1.08 | 11.23 | 67.72 | 1.58 | 1.38 | 0.166 | 35.48 |
| 12.00 | 28.13 | 1.58 | 18.88 | 0.72 | 1.17 | 12.48 | 62.59 | 2.27 | 2.03 | 0.199 | 40.15 |
| 13.00 | 24.10 | 1.24 | 22.09 | 0.82 | 1.56 | 16.18 | 54.74 | 2.94 | 2.71 | 0.296 | 44.10 |
| 14.00 | 31.30 | 1.18 | 22.96 | 0.68 | 1.46 | 18.86 | 49.17 | 6.78 | 5.01 | 0.384 | 48.76 |
| 15.00 | 35.16 | 0.81 | 28.47 | 0.79 | 1.48 | 30.26 | 32.83 | 4.54 | 4.60 | 0.922 | 54.04 |
| 16.00 | 36.88 | 0.39 | 16.30 | 4.61 | 0.47 | 41.24 | 5.88 | 14.43 | 12.96 | 7.016 | 57.70 |
| 17.00 | 33.20 | 5.83 | 2.71 | 16.14 | 0.89 | 10.25 | 6.54 | 25.60 | 23.31 | 1.566 | 59.86 |
| 18.00 | 32.68 | 10.38 | 5.42 | 22.58 | 2.11 | 8.33 | 2.97 | 23.73 | 16.06 | 2.803 | 61.93 |
| 19.00 | 20.58 | 12.56 | 7.04 | 20.67 | 2.54 | 9.96 | 4.75 | 21.42 | 14.35 | 2.099 | 63.14 |
| 20.00 | 17.12 | 12.71 | 7.61 | 19.24 | 2.32 | 10.33 | 5.14 | 22.67 | 15.55 | 2.009 | 64.24 |

With the exception of a brief period between 17-22 percent silicon conversion, Total Hydrocarbon (HC) formation in Example 9B (Table 18) showed a decreasing trend over the course of the twenty hour experiment. This is opposite to what was observed in Example 9A. Additionally, the ratio of lower boiling hydrocarbons to those boiling greater than 75° C. averaged 0.68 during the experiment. Accordingly, it can be concluded that addition of tetraglyme prevented the decomposition of Calflo™ LT and improved the activity, selectivity and stability of the slurry-phase Direct Synthesis of methylchlorosilanes from cyclone fines.

TABLE 18

DATA FOR EXAMPLE 9B: WITH TETRAGLYME ADDITIVE

| Time, h | Sample Weight, g | M2H, % | MH, % | Siltet, % | M, % | T, % | D, % | HC, % | HVS, % | T/D | Si Conv., % |
|---|---|---|---|---|---|---|---|---|---|---|---|
| 0.50 | 7.30 | 0.42 | 2.12 | 0.69 | 0.52 | 15.12 | 76.82 | 3.39 | 2.59 | 0.197 | 1.08 |
| 1.00 | 16.20 | 0.41 | 0.81 | 0.69 | 0.65 | 5.61 | 87.79 | 3.40 | 2.47 | 0.064 | 3.64 |
| 2.00 | 33.49 | 0.44 | 1.38 | 0.61 | 0.62 | 4.14 | 88.89 | 3.14 | 2.15 | 0.047 | 8.73 |
| 3.00 | 29.30 | 0.45 | 1.59 | 0.54 | 0.60 | 4.76 | 88.21 | 3.11 | 2.04 | 0.054 | 13.23 |
| 4.00 | 29.47 | 0.52 | 1.97 | 0.56 | 0.59 | 5.64 | 86.29 | 3.58 | 2.10 | 0.065 | 17.74 |
| 5.00 | 25.82 | 0.80 | 2.45 | 0.58 | 0.64 | 6.43 | 83.08 | 4.98 | 2.50 | 0.077 | 21.75 |
| 6.00 | 28.50 | 0.93 | 1.94 | 0.52 | 0.80 | 6.81 | 86.29 | 2.21 | 2.08 | 0.079 | 26.21 |
| 7.00 | 26.85 | 1.15 | 1.93 | 0.45 | 0.94 | 6.87 | 86.41 | 1.94 | 1.76 | 0.079 | 30.64 |
| 8.00 | 23.42 | 1.60 | 2.00 | 0.40 | 1.37 | 7.88 | 84.70 | 1.74 | 1.53 | 0.093 | 34.51 |
| 9.00 | 29.72 | 1.39 | 1.90 | 0.35 | 1.15 | 7.02 | 86.35 | 1.55 | 1.36 | 0.081 | 39.42 |
| 10.00 | 28.42 | 1.31 | 2.09 | 0.30 | 0.98 | 6.51 | 87.25 | 1.34 | 1.15 | 0.075 | 44.17 |
| 11.00 | 28.52 | 1.42 | 2.46 | 0.35 | 0.96 | 6.57 | 86.79 | 1.26 | 1.03 | 0.076 | 48.91 |
| 12.00 | 26.60 | 1.38 | 2.62 | 0.25 | 0.91 | 6.49 | 86.97 | 1.21 | 0.96 | 0.075 | 53.37 |
| 13.00 | 21.87 | 1.30 | 2.71 | 0.27 | 0.85 | 7.12 | 86.32 | 1.26 | 1.03 | 0.082 | 57.12 |
| 14.00 | 27.70 | 1.34 | 2.94 | 0.21 | 0.84 | 7.19 | 86.48 | 1.14 | 0.64 | 0.083 | 61.79 |
| 15.00 | 26.60 | 0.98 | 2.68 | 0.28 | 0.80 | 9.05 | 85.09 | 1.00 | 0.82 | 0.106 | 66.16 |
| 16.00 | 20.97 | 0.67 | 2.39 | 0.37 | 1.04 | 15.27 | 78.89 | 1.58 | 1.11 | 0.194 | 69.58 |
| 17.00 | 11.08 | 0.36 | 2.46 | 0.37 | 1.22 | 28.89 | 65.11 | 1.34 | 1.19 | 0.444 | 71.17 |
| 18.00 | 8.83 | 0.23 | 2.02 | 0.36 | 1.00 | 40.43 | 54.27 | 1.41 | 1.27 | 0.745 | 72.34 |
| 19.00 | 6.04 | 0.19 | 1.78 | 0.42 | 0.74 | 52.36 | 43.70 | 0.77 | 0.70 | 1.198 | 73.04 |
| 20.00 | 2.51 | 0.06 | 1.14 | 0.52 | 0.50 | 65.81 | 31.16 | 0.48 | 0.74 | 2.112 | 73.20 |

Example 10

This Example illustrates the use of turpentine to reduce solvent decomposition (hydrocarbon formation) and maintain good selectivity to $(CH_3)_2SiCl_2$ during the Direct Synthesis of methylchlorosilanes from cyclone fines in the aliphatic solvent, Calflo™ LT. Turpentine contains terpenes, among which are α-pinene, β-pinene, carene, camphene, dipentene and terpinolene. Example 9A was the control experiment for this Example.

The experiment was done in Reactor B using the procedure described above for Example 9B. Turpentine was delivered by a syringe pump, which was connected to the methyl chloride feed line such that a liquid additive could be continually fed into the reactor during the experiment. The reactor was charged with 420 g of high boiling Calflo™ LT oil, 0.9 g of SAG-47 antifoam and 140 g of the same batch of cyclone fines, which contained 1.3 wt % aluminum and 75% silicon. The reactors were heated to 300° C. under nitrogen and agitated at 445 rpm. The syringe pump was charged with turpentine, which was introduced at 0.5 ml/hr into the methyl chloride feed to the reactor. Methyl chloride was fed at 450 ml/min throughout the 28 hour run. The data are summarized in Table 19.

Table 17 shows that dimethyldichlorosilane (D) content in the hourly samples of Example 9A followed a decreasing trend between 5 and 64 percent silicon conversion. A steady-state was never established. Moreover, T/D increased beyond 0.1 after about 25 percent silicon conversion and reached ~0.4 at 49 percent silicon conversion. In contrast, T/D averaged 0.098 during the first 25 hours (~70 percent Si conversion) of Example 10 (see Table 19). Dimethyldichlorosilane (D) content in the hourly samples remained above 80 percent between 2 and 62 percent silicon conversion. It is clear that the continuous addition of turpentine improved the rate, selectivity and stability of the slurry-phase Direct Synthesis of methylchlorosilanes from cyclone fines.

In the control (Example 9A), methyldichlorosilane (MH) formation increased from 5 to 28 percent between 20 and 54 percent silicon conversion. With the addition of turpentine (Example 10), MH remained less than 5 percent up until about 55 percent silicon conversion (~21 hours).

Hydrocarbons are generated as a result of the decomposition of Calflo™ LT. This decomposition is probably catalyzed by $AlCl_3$ and other Lewis acids present in the reaction slurry. Paraffinic and olefinic hydrocarbons with six and fewer carbon atoms overlap the boiling range of the methylchlorosilane monomers and are likely to contaminate these compounds during fractional distillation. Hydrocarbons with normal boiling points greater than about 75° C. are also formed, or might have been volatilized from the Calflo™ LT solvent. Total hydrocarbon formation (HC) recorded in column 9 of Tables 17 and 19 is the sum of all hydrocarbons generated in the product samples, irrespective of their boiling points.

In the control (Example 9A, Table 17), total hydrocarbons fluctuated between 1-7 percent up to 54 percent silicon conversion. A rapid increase to 14-26 percent occurred thereafter. Most of this increase was attributable to hydrocarbons with normal boiling points lower than about 75° C. The ratio of these lower boiling hydrocarbons to those boiling greater than 75° C. increased from 0.73 to about 2.01 at silicon conversion greater than 58 percent.

Total Hydrocarbon (HC) formation in Example 10 (Table 18) showed a decreasing trend from about 3 percent to 0.8 percent during the first 26 hours (~72 percent silicon conversion) of the experiment. This is opposite to what was observed in Example 9A. Additionally, the ratio of lower boiling hydrocarbons to those boiling greater than 75° C. averaged 0.19 during the experiment. Accordingly, it can be concluded that addition of turpentine prevented the decomposition of Calflo™ LT and improved the activity, selectivity and stability of the slurry-phase Direct Synthesis of methylchlorosilanes from cyclone fines.

TABLE 19

DATA FOR EXAMPLE 10: WITH TURPENTINE ADDITIVE

| Time, h | Sample Weight, g | M2H, % | MH, % | Siltet, % | M, % | T, % | D, % | HC, % | HVS, % | T/D | Si Conv., % |
|---|---|---|---|---|---|---|---|---|---|---|---|
| 1.00 | 15.00 | 0.32 | 1.60 | 0.69 | 0.75 | 12.61 | 80.86 | 2.62 | 2.64 | 0.156 | 2.48 |
| 2.00 | 15.50 | 0.38 | 1.36 | 0.70 | 0.62 | 5.37 | 87.85 | 3.17 | 3.23 | 0.061 | 5.10 |
| 3.00 | 17.80 | 0.26 | 1.46 | 0.65 | 0.50 | 5.21 | 88.69 | 2.73 | 2.82 | 0.059 | 8.11 |
| 4.00 | 14.00 | 0.21 | 1.66 | 0.66 | 0.45 | 5.64 | 88.28 | 2.59 | 2.67 | 0.064 | 10.44 |
| 5.00 | 15.30 | 0.17 | 1.70 | 0.63 | 0.41 | 6.23 | 87.95 | 2.39 | 2.51 | 0.071 | 12.95 |
| 6.00 | 16.60 | 0.15 | 1.78 | 0.61 | 0.38 | 6.76 | 87.62 | 2.21 | 2.34 | 0.077 | 15.66 |
| 7.00 | 14.60 | 0.15 | 1.93 | 0.61 | 0.38 | 7.31 | 86.92 | 2.22 | 2.32 | 0.084 | 18.06 |
| 8.00 | 14.40 | 0.15 | 2.04 | 0.59 | 0.37 | 7.55 | 86.68 | 2.13 | 2.23 | 0.087 | 20.40 |
| 9.00 | 13.60 | 0.14 | 1.91 | 0.52 | 0.37 | 7.73 | 87.45 | 1.53 | 1.70 | 0.088 | 22.64 |
| 10.00 | 7.95 | 0.30 | 3.42 | 0.77 | 0.51 | 11.57 | 79.78 | 3.26 | 3.16 | 0.145 | 24.04 |
| 11.00 | 10.27 | 0.23 | 2.92 | 0.63 | 0.40 | 9.37 | 83.46 | 2.73 | 2.59 | 0.112 | 25.91 |
| 12.00 | 9.68 | 0.22 | 3.06 | 0.59 | 0.39 | 9.12 | 83.89 | 2.51 | 2.39 | 0.109 | 27.69 |
| 13.00 | 8.82 | 0.23 | 3.00 | 0.57 | 0.41 | 9.36 | 84.21 | 2.02 | 1.99 | 0.111 | 29.31 |
| 14.00 | 8.49 | 0.22 | 2.96 | 0.49 | 0.39 | 9.25 | 84.74 | 1.77 | 1.75 | 0.109 | 30.87 |
| 15.00 | 26.57 | 0.26 | 2.16 | 0.35 | 0.49 | 8.73 | 86.09 | 0.85 | 1.47 | 0.101 | 33.25 |
| 16.00 | 26.43 | 0.40 | 2.49 | 0.31 | 0.64 | 7.12 | 87.61 | 0.90 | 1.04 | 0.081 | 36.66 |
| 17.00 | 23.40 | 0.49 | 1.94 | 0.19 | 0.70 | 6.66 | 88.91 | 0.88 | 0.83 | 0.075 | 40.43 |
| 18.00 | 18.8 | 0.72 | 2.20 | 0.22 | 0.74 | 7.22 | 87.88 | 0.80 | 0.76 | 0.082 | 43.45 |
| 19.00 | 22.12 | 0.78 | 2.61 | 0.22 | 0.67 | 6.57 | 88.13 | 0.85 | 0.70 | 0.075 | 47.27 |
| 20.00 | 22.77 | 0.94 | 3.23 | 0.23 | 0.76 | 7.18 | 86.67 | 0.84 | 0.68 | 0.083 | 51.17 |
| 21.00 | 20.6 | 1.07 | 3.86 | 0.21 | 0.79 | 7.37 | 86.15 | 0.47 | 0.50 | 0.086 | 54.78 |
| 22.00 | 20.98 | 1.19 | 5.26 | 0.23 | 0.85 | 8.10 | 83.86 | 0.43 | 0.44 | 0.097 | 58.40 |
| 23.00 | 22.02 | 1.32 | 7.91 | 0.26 | 0.89 | 8.86 | 80.00 | 0.58 | 0.69 | 0.111 | 61.88 |
| 24.00 | 21.96 | 1.20 | 10.74 | 0.43 | 0.90 | 9.88 | 75.72 | 0.89 | 1.02 | 0.130 | 65.47 |
| 25.00 | 23.30 | 0.93 | 13.16 | 0.49 | 1.02 | 13.18 | 69.57 | 1.30 | 1.53 | 0.189 | 69.19 |
| 26.00 | 18.70 | 0.37 | 9.80 | 0.29 | 1.49 | 24.03 | 62.72 | 0.90 | 1.14 | 0.383 | 71.79 |

TABLE 19-continued

DATA FOR EXAMPLE 10: WITH TURPENTINE ADDITIVE

| Time, h | Sample Weight, g | M2H, % | MH, % | Siltet, % | M, % | T, % | D, % | HC, % | HVS, % | T/D | Si Conv., % |
|---|---|---|---|---|---|---|---|---|---|---|---|
| 27.00 | 15.50 | 0.15 | 7.91 | 1.37 | 1.34 | 56.27 | 26.23 | 4.37 | 6.20 | 2.145 | 73.59 |
| 28.00 | 11.70 | 0.62 | 12.03 | 1.44 | 0.39 | 46.44 | 12.32 | 13.52 | 24.40 | 3.768 | 74.43 |

Example 11A and 11B

These Examples illustrate the use of Dowtherm® MX and tetraglyme in the slurry-phase Direct Synthesis of methylchlorosilanes from cyclone solids in Reactor C. Reaction was done at 295° C. and atmospheric pressure in Example 11A and at 295° C. and 2.02 bar (29.4 psia) in Example 11B. The gravimetric ratio of Dowtherm®MX to cyclone fines was 3.0 in both experiments. Tetraglyme usage was based on the aluminum concentration (1.44 wt %) of the cyclone fines. Both experiments had 0.53 mole Al in the cyclone solids. It was determined that a mole ratio of tetraglyme to aluminum of 0.2 was an effective initial level to illustrate the benefits of tetraglyme to reaction stability and selectivity. Overall, four aliquots of tetraglyme were added during the experiments of Examples 11A (94.8 g total) and 11B (118.5 g total).

Reactions were run over a three day period. The temperature was lowered to 150° C. overnight during which methyl chloride was replaced by nitrogen. Tetraglyme was added at the times shown in Table 20. The other reaction conditions and the quantities of materials used in the experiments are also summarized in Table 20. The experimental results are shown graphically in FIG. 2 (Example 11A) and FIG. 3 (Example 11B).

TABLE 20

Material Quantities and Reaction Conditions used in Examples 11A and 11B.

| | EXAMPLE 11A | EXAMPLE 11B |
|---|---|---|
| SOLVENT AMOUNT, g | 3024 | 2995.6 |
| | Dowtherm ® MX | Dowtherm ®MX |
| CYCLONE SOLIDS, g | 998 | 996 |
| SILICON CHARGED, g | 698.6 | 697.2 |
| TEMPERATURE ° C. | 295 | 295 |
| $CH_3Cl$, L/min | 1 | 2 |
| PRESSURE, bar | 1.01 | 2.02 |
| AGITATION, RPM | 300 | 300 |
| SAG ® 47 Antifoam | 10.2 g | 10.5 g |
| TETRAGLYME ADDITION | 23.7 g at 4.53 h, 28.50 h, 45.74 h and 68.75 h | 47.4 g at the outset, 23.7 g at 4.87 h, 8.85 h and 11.78 h |
| REACTION DURATION | 21.13 h | 14.60 |
| TOTAL MCS CRUDE | 2579.9 g | 2477.7 |

FIG. 2 shows the concentrations of the principal methylchlorosilane monomers in the crude reaction product as a function of silicon conversion. Concentration of $(CH_3)_2SiCl_2$ (D) remained in the range, 82-92%, between 4.5 and 74 percent silicon conversion. The steady-state region was 4.5-70 percent silicon conversion and average D was 90.26±0.96%. Steady-state $CH_3SiCl_3$ (T) was 5.37±0.54%. T/D was 0.062±0.011 during steady-state. $CH_3SiHCl_2$ (MH) averaged 2.81±0.72% between 4.5 and 74 percent silicon conversion.

The higher pressure used in Example 11B resulted in a higher average MCS crude formation rate ((2477.7 g/14.60 h)=169.71 g/h) compared to that of Example 11A ((2579.9 g/21.13 h)=122.10 g/h). FIG. 3 shows that $(CH_3)_2SiCl_2$(D) remained above 80% up to about 45% silicon conversion. The average value was 85.07±3.82%. Average $CH_3SiCl_3$ (T) was 6.82±1.21% and T/D was 0.078±0.015 in the same silicon conversion range. The decline in D beyond 50 percent silicon conversion was matched by a larger increase in MH than T. As a result, (D+MH) averaged 89.81±3.02% up to about 65% silicon conversion. In both Example 11A and 11B, T/D and T/(D+MH) values were less than 0.2 up to at least sixty-five percent silicon conversion. Altogether, the data show that stable slurry-phase Direct Synthesis of methylchlorosilanes, selective to D, was realized when methyl chloride reacted with cyclone fines at 295° C. and 1-2 bar in Dowtherm®MX containing tetraglyme.

Examples 12A and 12B

This Example illustrates the improvements in selectivity and stability of the slurry-phase Direct Synthesis of methylchlorosilanes from cyclone fines brought about by the addition of diphenylamine to the reaction mixture. Experiments were done at 2:1 solvent/solids ratio in Therminol® 62 in Reactor A under the conditions used in Example 5G. Example 12A was the control reaction (same as Example 5G) without diphenylamine. The data are summarized in Table 21.

TABLE 21

Direct MCS Synthesis with Cyclone Fines in Therminol ® 62 with (Example 12B) and without (Example 12A) $(C_6H_5)_2NH$

| EX | Time (h) | % Si Conv. | % $HSiCl_3$ | % $SiCl_4$ | % $M_2H$ | % MH | % M | % T | % D | % HC | T/D |
|---|---|---|---|---|---|---|---|---|---|---|---|
| 12A | 6.2 | 29.7 | 23.94 | 1.69 | 0.51 | 28.9 | 0.48 | 15.71 | 23.24 | 4.42 | 0.68 |
| 12B | 6.0 | 20.8 | 0.1 | 0.24 | 0.77 | 8.99 | 0.86 | 9.44 | 75.14 | 0.57 | 0.13 |

As has been illustrated above in Example 5G, slurry phase Direct MCS synthesis with cyclone fines performs poorly in Therminol®62 in 2:1 solvent-to-solid ratio. Although MCS monomers were the major products at the beginning of the reaction, the $(CH_3)_2SiCl_2$ (D) yield dropped from 60% at the beginning to 16% at the end of 3 hours. Simultaneously, methyldichlorosilane (MH), silicon tetrachloride and methyltrichlorosilane (T) were produced in increasing amounts. Trichlorosilane (TCS) was the most abundant of the reaction products after 3 hours (up to 30%) with various other unknown products.

The data for Example 12B shows that addition of 2.5 weight percent (based on the weight of cyclone fines) diphenylamine improved T/D from 0.68 to 0.13 and D from 23.24% to 75.14%. Notably, TCS, $SiCl_4$, MH, T and hydrocarbons (HC) were all significantly reduced.

Examples 13A, 13B, and 13C

These Examples illustrate the reuse of solvent FDA-22™ and polydimethylsiloxane additive in the slurry-phase Direct Synthesis of methylchlorosilanes from cyclone solids. Reactor C was fitted with the anchor-shaped impeller and used in these experiments. Reaction 13A was done with fresh solvent at 300° C. and 2.02 bar (29.4 psia). Reactions 13B and 13C were done with previously used solvent at 300° C. and 3.04 bar (44.0 psia). The gravimetric ratio of FDA-22™ to cyclone fines was 3.0 in all three experiments. The polydimethylsiloxane used was Momentive Element 14™ PDMS-5A (5 Cst, $MD_8M$) and the usage was based on the aluminum concentration (1.94 wt %) of the cyclone fines. The experiments had 0.74, 0.73, and 0.76 mole Al in the cyclone solids, respectively. It was determined that a mass ratio of polydimethylsiloxane to aluminum of 15 was an effective initial level to illustrate the benefits of the polydimethylsiloxane additive to reaction stability and selectivity. In all three reactions, aliquots of polydimethylsiloxane were added at the start and later at intervals of 10% silicon conversion as determined from the GC analyses of the crude samples.

Reactions were run over a two day period. The temperature was lowered to 150° C. overnight during which methyl chloride was replaced by nitrogen. Polydimethylsiloxane additive was added as shown in Table 22. The other reaction conditions and the quantities of materials used in the experiments are also summarized in Table 22.

TABLE 22

Material Quantities and Reaction Conditions used in Examples 13A, 13B, and 13C.

| | EXAMPLE 13A | EXAMPLE 13B | EXAMPLE 13C |
|---|---|---|---|
| SOLVENT AMOUNT, g | FDA-22 ™, 3076 | FDA-22 ™, 3038 | FDA-22 ™, 3155 |
| SOLVENT, FRESH or REUSED | FRESH | REUSED | REUSED |
| CYCLONE SOLIDS, g | 1025 | 1013 | 1049 |
| SILICON CHARGED, g | 717.7 | 708.9 | 734.6 |
| TEMPERATURE ° C. | 300 | 300 | 300 |
| $CH_3Cl$, L/min | 3 | 3 | 3 |
| PRESSURE, bar | 2.02 | 3.04 | 3.04 |
| AGITATION, RPM | 200 | 200 | 200 |
| SAG 47 Antifoam | 15.2 g | 13.8 | 19.8 g |
| Polydimethylsiloxane Addition | 10 aliquots average 34.2 g at 1 h:15 min intervals | 8 aliquots average 45.6 g at 1 h:22 min intervals | 11 aliquots average 30.1 g at 1 h:05 min intervals |
| REACTION DURATION | 12.48 h | 10.5 h | 10.25 |
| SILICON CONVERSION | 72.95% | 73.7% | 75.3% |
| TOTAL MCS CRUDE | 2409.8 g | 2396.6 g | 2477.7 |

Table 23 shows the concentration of the major components in the accumulated crude from the experiments of Examples 13A, 13B, and 13C. Notably, when polydimethylsiloxane was used as an additive, its decomposition products, such as hexamethyldisiloxane, were not detected in the GC analysis of the MCS crude.

TABLE 23

Composition of Methylchlorosilane Crude from Examples 13A, 13B, and 13C.

| EX | FDA-22 ™ | Si Conversion, % | D, % | T, % | M, % | MH, % | M2H, % | T/D |
|---|---|---|---|---|---|---|---|---|
| 13A | FRESH | 72.95 | 81.6 | 9.9 | 3.7 | 2.3 | 0.67 | 0.12 |
| 13B | REUSED | 73.7 | 74.9 | 12.6 | 6.6 | 4.0 | 0.48 | 0.17 |
| 13C | REUSED | 75.3 | 77.4 | 11.1 | 5.8 | 3.9 | 0.49 | 0.14 |

The data show that acceptable rates, silicon conversion and selectivity to dimethyldichlorosilane were realized both with fresh and previously used solvent. The higher pressures used in Example 13B and 13C resulted in a higher average MCS crude formation rates ((2396.6 g/10.5 h)=228.2 g/h in Example 13B; (2477.7 g/10.25 h)=241.7 g/h in Example 13C, respectively, compared to that of Example 13A (2409.8 g/12.48 h)=193.1 g/h.

Examples 14A, 14B

These Examples illustrate the use of Calflo-LT™ and tetraglyme in the slurry-phase Direct Synthesis of methylchlorosilanes from cyclone solids in Reactor C. Reaction was done at 300° C. and 1.01 bar (14.7 psia). The gravimetric ratio of Calflo-LT™ to cyclone fines was 3.0 in both experiments. Tetraglyme usage was based on the aluminum concentration (1.44 wt %) of the cyclone fines. The experiments had 0.53 and 0.63 mole Al in the cyclone solids, respectively. The initial mole ratio of tetraglyme to aluminum was 1.23 in Example 14A and 1.05 in Example 14B. Overall, four aliquots of tetraglyme were added during the experiment.

Reactions were run over a four day period. The temperature was lowered to 150° C. overnight during which methyl chloride was replaced by nitrogen. Tetraglyme was added as shown in Table 24. The other reaction conditions and the quantities of materials used in the experiments are also summarized in Table 24.

TABLE 24

Material Quantities and Reaction Conditions used in Examples 14A and 14B.

|  | EXAMPLE 14A | EXAMPLE 14B |
|---|---|---|
| SOLVENT AMOUNT, g | Calflo LT ™, 2952 | Calflo LT ™, 3552 |
| CYCLONE SOLIDS, g | 984 | 1184 |
| SILICON CHARGED, g | 688.8 | 828.9 |
| TEMPERATURE ° C. | 300 | 300 |
| CH$_3$Cl, L/min | 1.5 | 1.0 |
| PRESSURE, bar | 1.01 | 1.01 |
| AGITATION, RPM | 300 | 300 |
| SAG 47 Antifoam | 9.7 g | 10.0 |
| TETRAGLYME ADDITION | 23.4 g aliquots at 2 h:05 min, 8 h:25 min, 16 h:22 min, 22 h:35 min | 27 g aliquots at 2 h:30 min, 10 h:45 min & 19 h:10 min. 13.5 g at 28 h:20 min |
| REACTION DURATION, h | 29.5 | 29.0 |
| SILICON CONVERSION, % | 65.6 | 64.2 |
| TOTAL MCS CRUDE, g | 2121.0 | 2078.8 |

In Example 14A, concentration of (CH$_3$)$_2$SiCl$_2$ (D) remained in the range, 84.4-91.4%, between 3.2 and 62.4 percent silicon conversion. The steady-state region was 4.9-60.4% silicon conversion. In Example 14A, at silicon conversion beyond 60.4%, the concentration of D in the crude declined and the concentration of T in the crude increased. In Example 14B, concentration of (CH$_3$)$_2$SiCl$_2$ (D) remained in the range, 83.7-91.2%, between 4.28 and 64.2% silicon conversion. The experiment shown in Example 14B was terminated before crude quality began to decline. Table 25 gives the average crude composition in the steady-state region for Examples 14A and 14B.

TABLE 25

STEADY-STATE COMPOSITION OF THE MCS CRUDE FROM EXAMPLES 14A AND 14B.

| EX | Si Conversion, % | D, % | T, % | M, % | MH, % | M2H, % | T/D |
|---|---|---|---|---|---|---|---|
| 14A | 4.9-60.4 | 89.9 | 6.8 | 0.52 | 1.78 | 0.43 | 0.076 |
| 14B | 4.28-64.2 | 87.3 | 8.1 | 0.5 | 2.7 | 0.41 | 0.093 |

The lower pressures and methyl chloride flow rate used in Examples 14A and 14B resulted in a lower average MCS crude formation rate as compared to Examples 13A, 13B, and 13C. Example 14A crude formation was ((2121 g/29.5 h)=71.9 g/h. Example 14B crude formation was (2078.8 g/29.0 h)=71.1 g/h compared to those of Example 13A, 13B, and 13C of 193.1 g/h, 228.1 g/h, 241.7 g/h, respectively.

Example 15

This Example illustrates the use of FDA-22™ without using a stabilizing additive in the slurry-phase Direct Synthesis of methylchlorosilanes from cyclone solids in Reactor C. Reaction was done at 300° C. and 1.03 bar (~15 psia). The gravimetric ratio of FDA-22™ to cyclone fines was 3.0 in both experiments. The aluminum concentration in the cyclone fines was 1.96% and the experiment had 0.36 mole Al in the cyclone solids.

The reactions were run over a three day period. The temperature was lowered to 150° C. overnight during which methyl chloride was replaced by nitrogen Table 26.

TABLE 26

Material Quantities and Reaction Conditions used in Examples 15.

|  | EXAMPLE 15 |
|---|---|
| SOLVENT AMOUNT, g | FDA-22 ™, 2952 |
| CYCLONE SOLIDS, g | 498.7 |
| SILICON CHARGED, g | 349.1 |
| TEMPERATURE ° C. | 300 |
| $CH_3Cl$, L/min | 1.0 |
| PRESSURE, bar | 1.01 |
| AGITATION, RPM | 200 |
| SAG ® 47 Antifoam, g | 4.8 |
| REACTION DURATION, h | 22.9 |
| SILICON CONVERSION, % | 65.9 |
| TOTAL MCS CRUDE, g | 1065.30 |

The concentrations of the principal methylchlorosilane monomers in the crude reaction product as a function of silicon conversion are summarized in Table 27. In Example 15, the concentration of $(CH_3)_2SiCl_2$ (D) remained in the range, 83.6-88.5%, between 4.6 and 22.8 percent silicon conversion. For silicon conversion greater than 22.8%, the quality of the MCS crude declined. The experiment was stopped at 65.8% silicon conversion. In the range from 22.8% to 62.8% silicon conversion, the concentration of $(CH_3)_2SiCl_2$ (D) in the MCS crude dropped at a steady rate to 45.3%. Over the same range of silicon conversion, the $CH_3SiCl_3$ (T) increased gradually from 7.3% to 39.2%. The concentration of $CH_3SiHCl_2$ (MH) in the same range went from 7.5% at 22.8% silicon conversion to a maximum of 24.1% before starting to decline. At silicon conversions greater than 62.8%, quality of the MCS crude more rapidly declined and is the reason the run was terminated at 65.8% conversion.

TABLE 27

COMPOSITION OF MCS CRUDE FOR EXAMPLE 15.

| EX | Si Conversion, % | D, % | T, % | M, % | MH, % | M2H, % | T/D |
|---|---|---|---|---|---|---|---|
| 15 | 4.6-22.8 | 86.2 | 7.0 | 1.1 | 5.4 | 0.37 | 0.08 |
| 15 | >22.8-62.8 | 59.9 | 18.2 | 2.6 | 18.8 | 0.56 | 0.303 |
| 15 | 4.6-62.8 | 69.5 | 14.1 | 2.0 | 13.9 | 0.49 | 0.203 |

Comparing Example 15 to Examples 14A and 14B illustrates how using the additive tetraglyme stabilized the slurry-phase Direct Synthesis of methylchlorosilanes. In Example 15, without tetraglyme stabilizer, the steady-state period with good selectivity to D ended at 22.8% silicon conversion and the overall yield of D in the MCS crude was 69.5%. On the other hand, Examples 14A and 14B show that addition of tetraglyme extended the steady-state period with good selectivity to D to beyond 60% silicon conversion. The result of this was MCS crude with over 87% concentration of D and T/D 0.07-0.09.

Examples 16A, 16B

These Examples illustrate the use of the fresh and re-used solvents composed of the eutectic blend of Biphenyl and Diphenyl Ether and Momentive Element 14™ PDMS-5A in the slurry-phase Direct Synthesis of methylchlorosilanes from cyclone solids in Reactor C. Reaction 16A was done using fresh solvent at 240° C. and 3.04 bar (44.1 psia) and 4.05 bar (58.1 psia). Reaction 16B was done with recovered solvent at 240° C. and 3.04 bar (44.1 psia). The gravimetric ratio of the eutectic blend to cyclone solids was 2.0 in experiment 16A and 1.89 in Experiment 16B. The Momentive Element 14™ PDMS-5A usage was based on the aluminum concentration (1.25 wt %) of the cyclone fines. The experiments had 0.689, 0.667 mole Al in the cyclone solids, respectively. It was determined that a mass ratio of polydimethylsiloxane to aluminum of 15 was an effective initial level to illustrate the benefits of polydimethylsiloxane to reaction stability and selectivity. In both reactions, aliquots of polydimethylsiloxane were added at the start and later on at regular intervals. In Experiment 16A, the interval was approximately every 6% of silicon conversion. In Experiment 16B the interval was every 3.5% of silicon conversion.

The eutectic blend of Biphenyl and Diphenyl Ether used in Experiment 16A was mixed in the lab from materials purchased from Sigma Aldrich. The reaction residue from Experiment 16A was further processed by vacuum stripping to separate the liquid from the spent solid fines. This was done in Reactor C at 0.133 bar (100 mmHg) with hot oil circulating through the Reactor C jacket at temperature ranging from 220° C. to 280° C. The vacuum stripping produced liquid distillate and dry solid powder. The liquid distillate from Experiment 16A is the eutectic blend reused in Experiment 16B.

Experiment 16A was run over a three day period and Experiment 16B over a four day period. The temperature was lowered to 150° C. overnight during which methyl chloride was replaced by nitrogen. Momentive Element 14™ PDMS-5A was added as shown in Table 28. The other reaction conditions and the quantities of materials used in the experiments are also summarized in Table 28.

TABLE 28

Material Quantities and Reaction Conditions used in Examples 16A and 16B.

|  | EXAMPLE 16A | EXAMPLE 16B |
|---|---|---|
| SOLVENT AMOUNT, g | (BP + DPE)* 2973 | (BP + DPE)* 2730 |
| CYCLONE SOLIDS, g | 1488 | 1441 |
| SILICON CHARGED, g | 1042 | 1008.7 |
| TEMPERATURE ° C. | 240 | 240 |
| $CH_3Cl$, L/min | 2.0 to 2.50 | 2.25 to 2.50 |
| PRESSURE, bar | 3.04-4.05 | 3.04 |
| AGITATION, RPM | 300 | 300 |
| SAG ® 100 Antifoam, g | 29.8 | 30.5 |
| POLYDIMETHYLSILOXANE ADDITION | 13 aliquots averaging 25.7 g | 21 aliquots averaging 14.9 g |
| REACTION DURATION, h | 22.5 | 23.6 |
| SILICON CONVERSION | 78.0 | 71.7 |
| TOTAL MCS CRUDE, g | 3695.0 | 3305.0 |

*(BP + DPE) = Biphenyl - Diphenyl Ether eutectic blend

Table 29 shows the concentration of the major components in the crude from for Examples 16A, 16B.

TABLE 29

RESULTS OF THE EXPERIMENTS OF EXAMPLES 16A AND 16B.

| EX | D, % | T, % | M, % | MH, % | M2H, % | T/D |
|---|---|---|---|---|---|---|
| 16A | 82.0 | 7.5 | 4.5 | 4.0 | 1.2 | 0.09 |
| 16B | 87.0 | 6.8 | 4.0 | 1.2 | 0.7 | 0.08 |

Comparing the results of Experiment 16B using reused solvent with 16A using fresh solvent illustrates how using reused solvent has not had a negative effect on the quality of the MCS crude produced by the slurry fines Direct Process.

Example 17 (Comparative)

This example illustrates the use of Momentive Element 14™ PDMS-5A as the solvent in the slurry-phase Direct Synthesis of methylchlorosilanes from cyclone solids in Reactor C. The experiment was done using fresh Momentive Element 14™ PDMS-5A solvent at 280° C. and 3.04 bar (44.1 psia). The gravimetric ratio of the solvent to cyclone solids was 3.0. The aluminum concentration (1.94 wt %) of the cyclone fines. The experiment had 0.754% Al in the cyclone solids. It was run on one day. The reaction conditions and the quantities of materials used in the experiment are summarized in Table 30.

TABLE 30

Material Quantities and Reaction Conditions used in Example 17.

| | EXAMPLE 17 |
|---|---|
| SOLVENT AMOUNT, g | PDMS-5A, 3146 |
| CYCLONE SOLIDS, g | 1048 |
| SILICON CHARGED, g | 733.7 |
| TEMPERATURE ° C. | 280 |
| $CH_3Cl$, L/min | 3.0 |
| PRESSURE, bar | 3.04 |
| AGITATION, RPM | 300 |
| SAG ® 47 Antifoam | 15.6 |
| REACTION DURATION, h | 6.6 |
| SILICON CONVERSION % | 35.7 |
| TOTAL MCS CRUDE, g | 1189.9 |

Example 17 was terminated after a silicon conversion of 35.7%. The reaction was terminated early due to significant solvent decomposition. On average, 45% of each sample taken in Experiment 17 was material with higher boiling point than $(CH_3)_2SiCl_2$ (D). Table 31 shows the concentration of the major components in the crude from for Example 17. In contrast to the experiments wherein polydimethylsiloxane was used as an additive (Examples 13A-13C and Examples 16A-16B), GC analysis of the MCS crude samples from Experiment 17 showed appreciable amounts of hexamethyldisiloxane $[(CH_3)_3Si]_2O$.

TABLE 31

COMPOSITION OF MCS CRUDE FOR EXAMPLE 17.

| EX | D, % | T, % | M, % | MH, % | M2H, % | T/D |
|---|---|---|---|---|---|---|
| 17 | 85.3 | 5.4 | 8.4 | 0.2 | 0.52 | 0.063 |

Examples 18A-18D

These Examples illustrate the slurry-phase Direct Synthesis of allyl trichlorosilane from allyl chloride and cyclone fines in Dowtherm® MX. Reactor A was used.

1050 g Dowtherm® MX and 350 g cyclone fines were charged to the reactor along with 4 g FF 170. The reaction mixture was sparged with 100 mL/min nitrogen, stirred at 500 rpm and heated to 260° C. Allyl chloride was introduced manually with a 30 ml syringe and 30.6 cm (12 inch) needle inserted through a serum cap in one of the 24/40 ports in the reactor head. In the experiment of Example 18A, 22 g allyl chloride was injected in 4 minutes. In Example 18B, the reactor temperature was lowered to 245° C. and 20 g allyl chloride was injected in 4 minutes. The results of the experiments are summarized in Table 32.

A 50 weight percent mixture of allyl chloride with methyl trichlorosilane was introduced in Examples 18C and 18D. Example 18C was run at 260° C. with 36 g of the mixture injected over 10 minutes. Example 18D was done at 245° C. with 20 g of the mixture injected in 4 minutes. The results of the experiments are summarized in Table 33.

TABLE 32

RESULTS OF THE EXPERIMENTS OF EXAMPLES 18A AND 18B

| EXAMPLE 18A, 260° C. | Weight Percent | EXAMPLE 18B, 245° C. | Weight Percent |
|---|---|---|---|
| Allyl Chloride | 54.45 | Allyl Chloride | 38.62 |
| Allyldichlorosilane (ADCS) | 1.19 | Allyldichlorosilane (ADCS) | 0.00 |
| Allyltrichlorosilane (ATCS) | 42.95 | Allyltrichlorosilane (ATCS) | 51.26 |
| Diallyldichlorosilane (DADCS) | 1.41 | Diallyldichlorosilane (DADCS) | 10.12 |
| ATCS/DADCS | 30.50 | ATCS/DADCS | 5.06 |
| ATCS/ADCS | 36.09 | ATCS/ADCS | ∞ |

TABLE 33

RESULTS OF THE EXPERIMENTS OF EXAMPLES 18C AND 18D

| EXAMPLE 18C, 260° C. | Weight Percent | EXAMPLE 18D, 245° C. | Weight Percent |
|---|---|---|---|
| Allyl Chloride | 34.02 | Allyl Chloride | 24.20 |
| Methyltrichlorosilane | 42.42 | Methyltrichlorosilane | 23.94 |
| Allyldichlorosilane | 1.32 | Allyldichlorosilane | 2.71 |
| Allyltrichlorosilane | 20.40 | Allyltrichlorosilane | 40.67 |
| Diallyldichlorosilane | 1.83 | Diallyldichlorosilane | 8.48 |
| ATCS/DADCS | 11.15 | ATCS/DADCS | 4.79 |
| ATCS/ADCS | 15.45 | ATCS/ADCS | 15.00 |

In all four experiments, formation of allyltrichlorosilane exceeded that of allyldichlorosilane and diallyldichlorosilane. These data are in contrast to those reported by Yeon, et al (*Organometallics*, vol 12 (1993), pp 4887-4891) for the stirred-bed Direct Synthesis of allychlorosilanes. In that report, allyltrichlorosilane production was less than either that of allyldichlorosilane or diallyldichlorosilane when allyl chloride was fed alone or admixed with hydrogen chloride.

Example 19

This Example illustrates the slurry-phase Direct Synthesis of allyltrichlorosilane and allyl dichlorosilane from allyl choride-HCl mixtures and cyclone fines in Calflo™ AF. Reactor A was used.

702 g Calflo™ AF and 213.8 g cyclone fines were charged to the reactor along with 2.5 g FF 170. The reaction mixture was sparged with 100 mL/min nitrogen, stirred at 500 rpm and heated to 235° C. After the reactor temperature reached to 235° C., hydrogen chloride was introduced to the reactor at the rate of 420 mL/min. Allyl chloride was pumped from a reservoir into an evaporator heated at 80° C., and then fed to the reactor as vapor. The experiment was terminated after 4.5 hr and a total of 660 mL allyl chloride was delivered to the reactor during the experimental time. Overall, 113.45 g HCl (4.63 mole) and 620.20 g allyl chloride (8.10 mole) were introduced into the reactor. The molar ratio, [Allyl chloride/HCl], was 1.75. The Product was collected and analyzed by GC every half an hour. 467.6 g crude product was collected and 50.1% silicon conversion was obtained from the available silicon in the cyclone fines. Table 34 summarizes the composition of the major silicon-containing products in the crude. Note that in the experiments of Examples 18 and 19, it was observed that the slurry had increased in weight during the reaction. This suggests formation of reaction products that were not discharged from the reactor at 235-260° C.

TABLE 34

COMPOSITION OF SAMPLES COLLECTED
IN THE EXPERIMENT OF EXAMPLE 19

| Time, h | ADCS, wt % | ATCS, wt % | DADCS, wt % | RATIO* | Si Conv., % |
|---|---|---|---|---|---|
| 1.00 | 39.63 | 40.44 | 2.58 | 31.03 | 4.32 |
| 1.50 | 40.01 | 46.56 | 4.03 | 21.48 | 7.82 |
| 2.00 | 42.80 | 45.65 | 3.74 | 23.65 | 12.36 |
| 2.50 | 47.42 | 39.57 | 4.48 | 19.42 | 18.07 |
| 3.00 | 48.23 | 38.47 | 4.59 | 18.89 | 25.72 |
| 3.50 | 46.79 | 39.83 | 5.04 | 17.19 | 34.07 |
| 4.00 | 45.77 | 38.99 | 3.89 | 21.79 | 43.65 |
| 4.50 | 21.06 | 43.98 | 2.34 | 27.79 | 50.13 |

*RATIO = (ADCS + ATCS)/DADCS

It is clear from the data of Table 34 that the crude product discharged during the slurry-phase Direct Synthesis of allyl chlorosilanes from cyclone fines and allyl chloride-HCl mixtures contains more allyldichlorosilane and allyltrichlorosilane than diallyldichlorosilane. The Ratio, (ADCS+ATCS)/(DADCS), was consistently greater than 15 and attained a maximum value greater than 30.

What is claimed is:

1. A process for the synthesis of organohalosilane monomers, comprising the steps of:
   (1) forming a slurry of cyclone fines, ultra fines and/or spent contact mass in a thermally stable solvent and reacting the agitated slurry with at least one organohalide of the formula $R^1X$ and optionally organohalosilane and/or hydrogen halide in the presence of an additive selected from the group consisting of dialkylpolyethers, podands, secondary amines, terpenes, diterpenes, triterpenes, nitrohydrocarbons, nitriles, hexamethyldisiloxane, polydimethylsiloxanes having a viscosity of from 5 to 100 cSt, and mixtures thereof for a reaction time and at a temperature and pressure sufficient to produce organohalosilane monomers having the formulae $R^1SiHX_2$, $R^1_2SiHX$, $R^1_3SiX$, $R^1SiX_3$, and $R^1_2SiX_2$ or mixtures thereof;
   wherein $R^1$ is a saturated or unsaturated aromatic group, a saturated or unsaturated aliphatic group, alkaryl group, or cycloaliphatic hydrocarbyl group, and X is a halogen; and
   (2) recovering said organohalosilane monomers from said solvent.

2. The process of claim 1, wherein $R^1$ is methyl, ethyl, phenyl, cyclohexyl, allyl, vinyl, methallyl, phenyl, or benzyl.

3. The process of claim 1 wherein the slurry is a slurry of cyclone fines and wherein $R^1$ is allyl or methallyl and the organohalosilane monomers are of the formulae $R^1SiX_3$ or mixtures of $R^1SiX_3$ and $R^1SiHX_2$ and wherein the optional hydrogen halide is present and where the molar ratio of allyl halide to hydrogen halide in the mixture of step (1) is greater than or equal to one.

4. The process of claim 1 wherein X is fluorine, chlorine, bromine, or iodine.

5. The process of claim 1, wherein the organohalide is selected from the group consisting of methyl chloride, methyl bromide, ethyl chloride, vinyl chloride, allyl chloride, chlorobenzene, and mixtures thereof.

6. The process of claim 1, wherein the solvent is selected from the group consisting of linear or branched paraffins, naphthenes, alkylated benzenes, dialkylated benzenes, aromatic ethers, polyaromatic hydrocarbons, hydrochloric acid and mixtures thereof.

7. The process of claim 1, wherein said additive is selected from the group consisting of tetra(ethyleneglycol)dimethyl ether, tri(ethyleneglycol)dimethyl ether, diphenylamine, hexamethyldisiloxane, polydimethylsiloxanes having a viscosity of from 5 to 100 cSt, turpentine, squalene, nitrobenzene, trivinylcyclohexane, adiponitrile, 1,6-dicyanohexane, and mixtures thereof.

8. The process of claim 1, wherein said temperature is greater than about 180° C.

9. The process of claim 1, wherein said temperature ranges from about 250° C. to about 450° C. when the organohalide is methyl chloride, methyl bromide, ethyl chloride and chlorobenzene.

10. The process of claim 1, wherein the reaction pressure ranges from about atmospheric pressure to about 10 atmospheres.

11. The process of claim 1, wherein the reaction time is within the range from about 0.1 to about 100 hours.

12. The process of claim 1, further comprising combining said slurry and said organohalide in the presence of a foam control agent.

13. The process of claim 1, further comprising the step of recovering the solvent for reuse in step (1).

14. The process of claim 1, further comprising introducing additional cyclone fines, ultra fines and/or spent mass into the reaction slurry after the initial charge has been partially or fully converted, and continuing the reaction with the organohalide to produce organohalosilane monomers without first recovering and/or remediating the solvent.

15. A process for the synthesis of organohalosilane monomers, comprising the steps of:
   (1) forming a slurry of cyclone fines, ultra fines and/or spent contact mass in a thermally stable solvent and reacting the agitated slurry with methyl chloride and optionally organohalosilane and/or hydrogen halide in the presence of tetraglyme for a reaction time and at a temperature of from 240° C. to about 350° C. and at a pressure of from about 1 to about 5 atmospheres to produce organohalosilane monomers having the formulae $R^1SiHX_2$, $R^1_2SiHX$, $R^1_3SiX$, $R^1SiX_3$, and $R^1_2SiX_2$ or mixtures thereof;
   wherein $R^1$ is methyl, and X is Cl; and
   (2) recovering said organohalosilane monomers from said solvent and wherein the initial solvent to solids gravimetric ratio is in the range from about 1 to about 3.

16. The process of claim 1 wherein the organohalide is allyl chloride, allyl bromide, methallyl chloride or methallyl bromide, and the reaction is conducted at about 200 to about 280° C.

17. The process of claim 16 wherein the organohalide is allyl chloride, initial solvent to solids gravimetric ratio is about 1 to about 3, the additives are methyltrichlorosilane, tetraglyme, or combinations thereof, the temperature is about 200 to about 280° C. and the pressure is about 1 to about 5 atmospheres.

18. The process of claim 16 wherein products of general formula, $R^1SiX_3$, and/or $R^1SiHX_2$, are produced with greater selectivity than al least one of the products of general formulae, $R^1_2SiX_2$, $R^1_3SiX$, $R^1_2SiXH$ and $R^1SiHX_2$ when $R^1$ is unsaturated.

19. The process of claim 1 wherein the products of the general formula $R^1_2SiX_2$ are produced with greater selectivity than products of the general formula $R^1SiX_3$ when $R^1$ is saturated.

* * * * *